United States Patent
Shaviv

(10) Patent No.: US 8,568,342 B2
(45) Date of Patent: Oct. 29, 2013

(54) DEVICES, SYSTEMS AND METHODS FOR SHORTENING MENSTRUAL PERIOD DURATION

(75) Inventor: Hilla Shaviv, Mevasseret Zion (IL)

(73) Assignee: GalMedics Biotech Ltd., Mevasseret Zion (IL)

(*) Notice: Subject to any disclaimer, the term of this patent is extended or adjusted under 35 U.S.C. 154(b) by 963 days.

(21) Appl. No.: 12/450,011

(22) PCT Filed: Mar. 9, 2008

(86) PCT No.: PCT/IL2008/000312
§ 371 (c)(1),
(2), (4) Date: Sep. 8, 2009

(87) PCT Pub. No.: WO2008/107902
PCT Pub. Date: Sep. 12, 2008

(65) Prior Publication Data
US 2010/0056963 A1    Mar. 4, 2010

Related U.S. Application Data

(60) Provisional application No. 60/893,387, filed on Mar. 7, 2007, provisional application No. 60/950,054, filed on Jul. 16, 2007.

(51) Int. Cl.
*A61H 1/00* (2006.01)
(52) U.S. Cl.
USPC ............................................. 601/46; 601/84
(58) Field of Classification Search
USPC ............... 601/46, 84, 148–150, 48; 604/358, 604/385.01, 385.17, 904
See application file for complete search history.

(56) References Cited

U.S. PATENT DOCUMENTS

| 3,669,100 | A | | 6/1972 | Csanad |
| 4,607,624 | A | | 8/1986 | Jefferson |
| 5,762,066 | A | * | 6/1998 | Law et al. ................. 600/439 |

(Continued)

FOREIGN PATENT DOCUMENTS

| DE | 20200504843 | 7/2005 |
| GB | 349679 | 6/1931 |
| GB | 236560 | 7/1980 |
| WO | WO 2008/107902 | 9/2008 |

OTHER PUBLICATIONS

International Preliminary Report on Patentability Dated Oct. 29, 2009 From the International Bureau of WIPO Re.: Application No. PCT/IL2008/000312.

(Continued)

*Primary Examiner* — Michael A. Brown

(57) ABSTRACT

Devices and systems for facilitating the flow of menses through the cervix and for shortening the duration of menstruation include a pressure oscillations generating unit insertable into a vagina and configured for delivering pressure oscillations and/or acoustic waves and/or shock waves to the vagina and cervix to change the flow properties of menses fluid. The pressure oscillations generating unit may include one or more vibratable or movable members for generating pressure oscillations which may be powered by an internal or external power source. The devices may optionally include an absorbing member or a menses collecting member. A method of menstruation duration shortening includes placing the device within the vagina and applying pressure oscillations to the vagina or to a vaginal chamber formed within the vagina for increasing the flow rate of menses and shortening menstruation duration.

32 Claims, 15 Drawing Sheets

(56) References Cited

U.S. PATENT DOCUMENTS

| | | | | |
|---|---|---|---|---|
| 5,782,779 A * | 7/1998 | Kilgore | | 601/70 |
| 6,058,932 A | 5/2000 | Hughes | | |
| 6,183,428 B1 | 2/2001 | Kilgore | | |
| 6,193,667 B1 | 2/2001 | Kensey | | |
| 6,193,677 B1 * | 2/2001 | Cady | | 601/1 |
| 6,540,665 B1 * | 4/2003 | Connolly | | 600/29 |
| 6,563,933 B1 * | 5/2003 | Niederdraenk | | 381/417 |
| 6,984,214 B2 * | 1/2006 | Fowler-Hawkins | | 601/46 |
| 2004/0097850 A1 * | 5/2004 | Plante | | 601/41 |
| 2006/0140924 A1 * | 6/2006 | Schroeder et al. | | 424/94.1 |

OTHER PUBLICATIONS

International Search Report Dated Apr. 3, 2009 From the International Searching Authority Re.: Application No. PCT/IL08/00312.

Written Opinion Dated Apr. 3, 2009 From the International Searching Authority Re.: Application No. PCT/IL08/00312.

Office Action Dated Apr. 6, 2011 From the Israel Patent Office Re. Application No. 200786 and Its Translation Into English.

Office Action Dated Aug. 31, 2012 From the State Intellectual Property Office of the People's Republic of China Re. Application No. 200880015219.1 and Its Translation Into English.

Communication Pursuant to Rules 70(2) and 70a(2) EPC Dated Jul. 18, 2013 From the European Patent Office Re. Application No. 08719937.8.

Supplementary European Search Report and the European Search Opinion Dated Jul. 1, 2013 From the European Patent Office Re. Application No. 08719937.8.

Translation of Office Action Dated May 30, 2013 From the State Intellectual Property Office of the People's Republic of China Re. Application No. 200880015219.1.

* cited by examiner

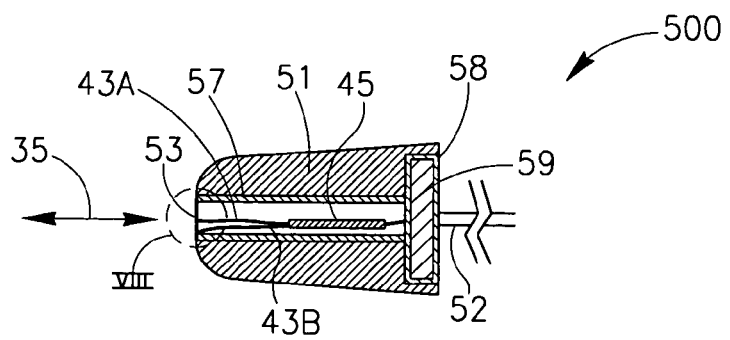
FIG. 7
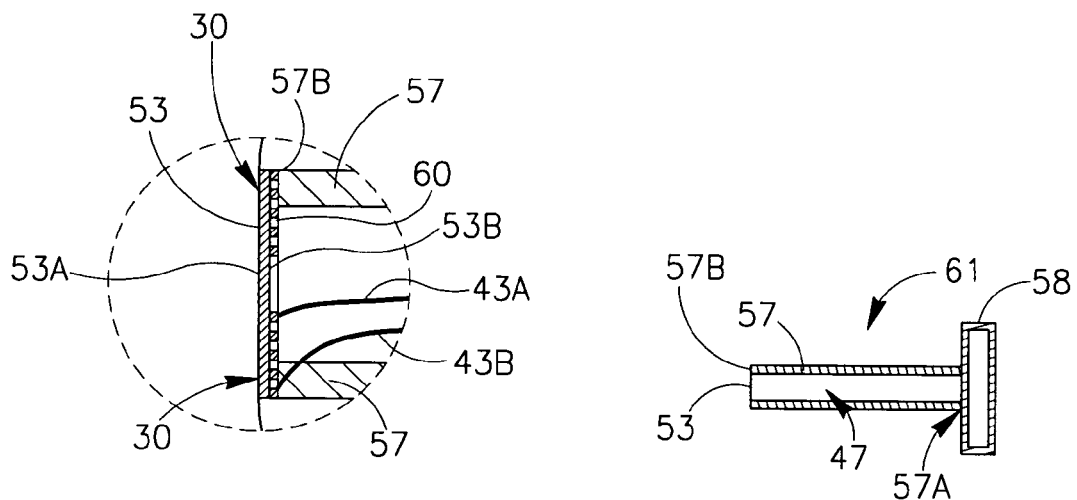
FIG. 8
FIG. 9
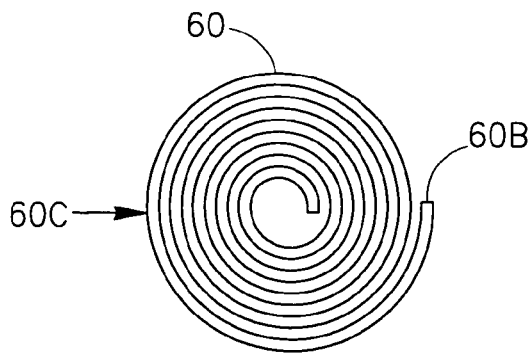
FIG. 10
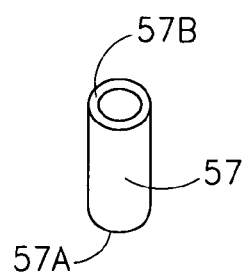
FIG. 11
FIG. 12
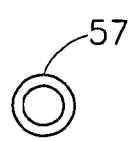
FIG. 13

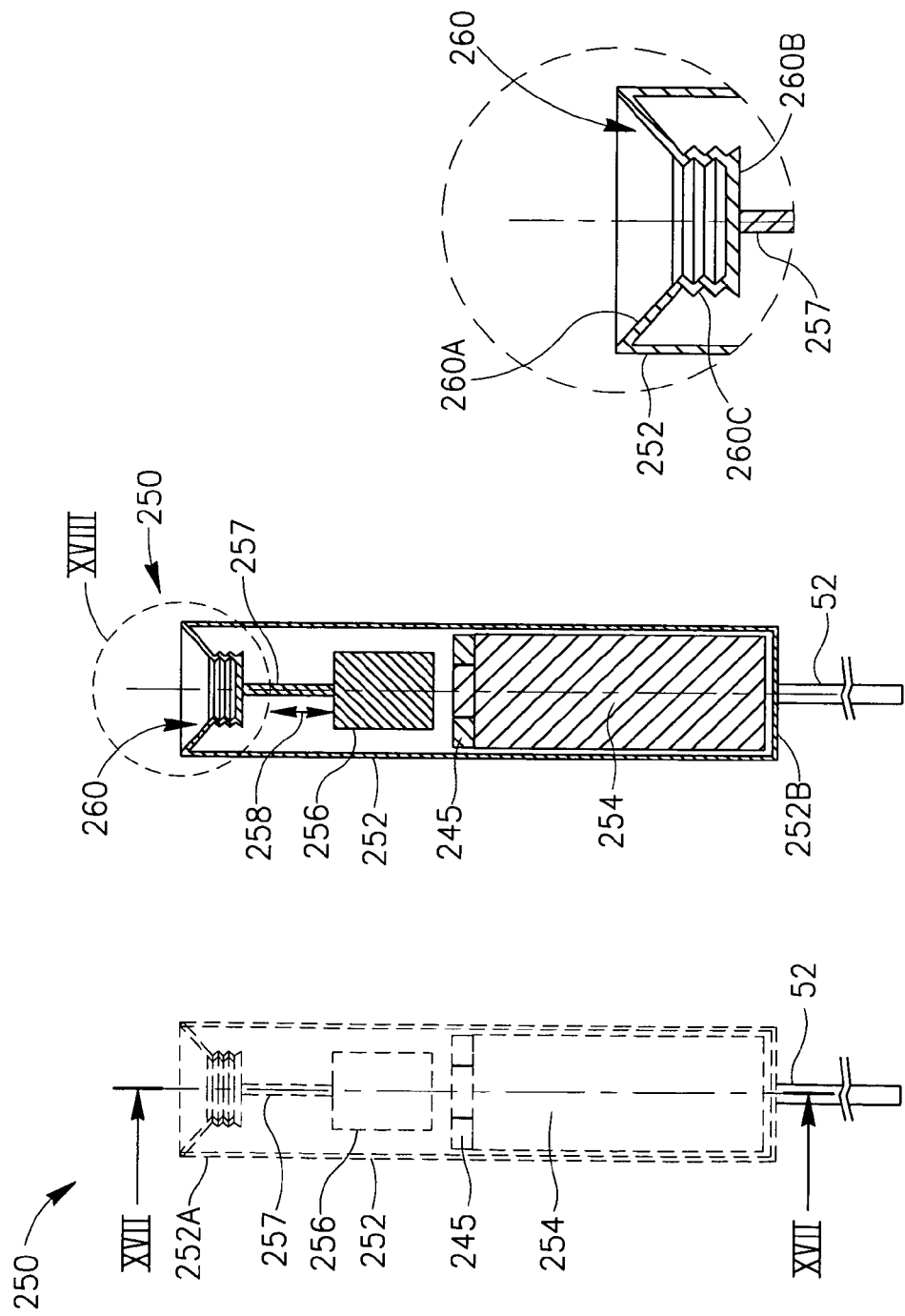

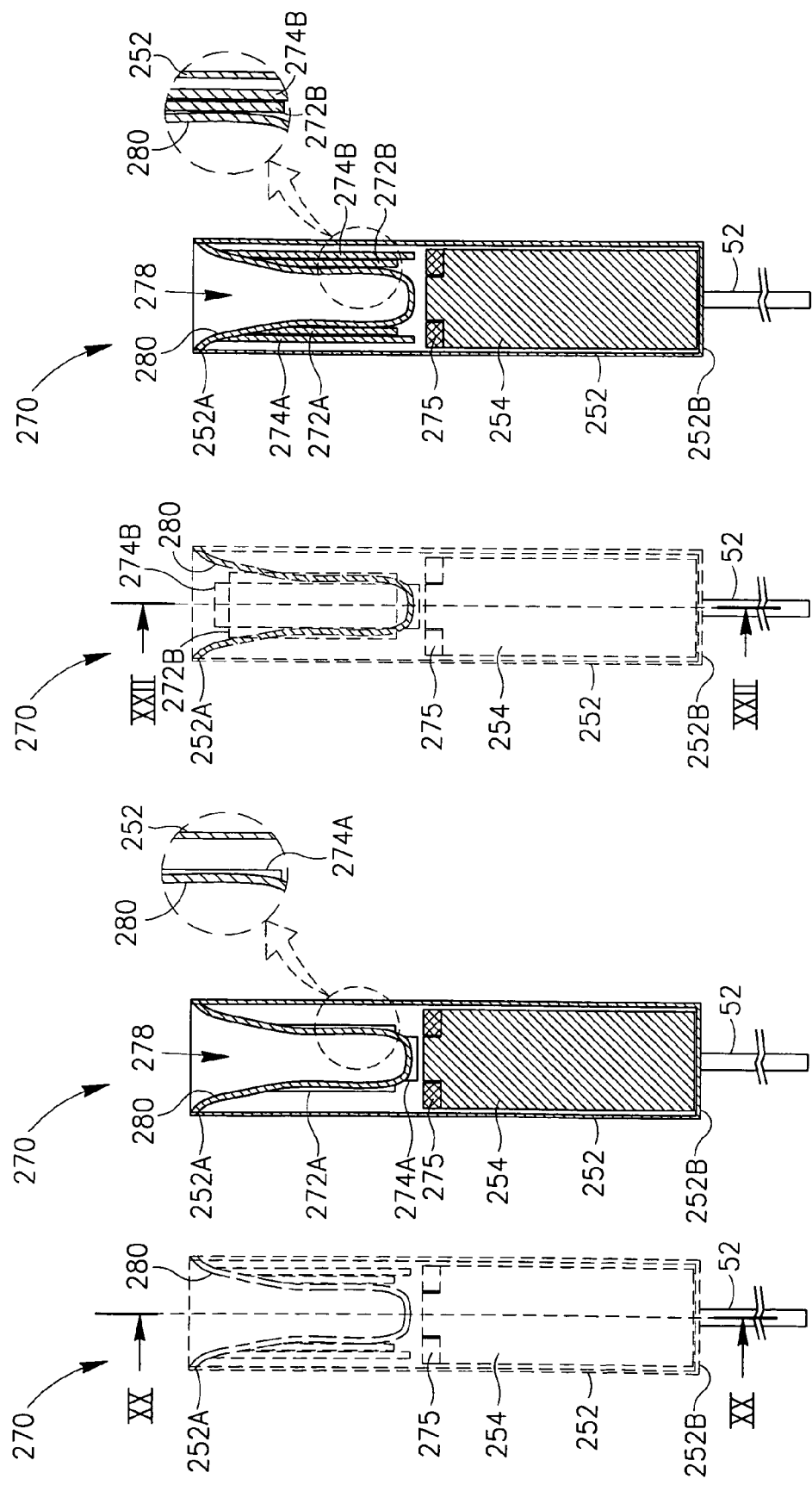

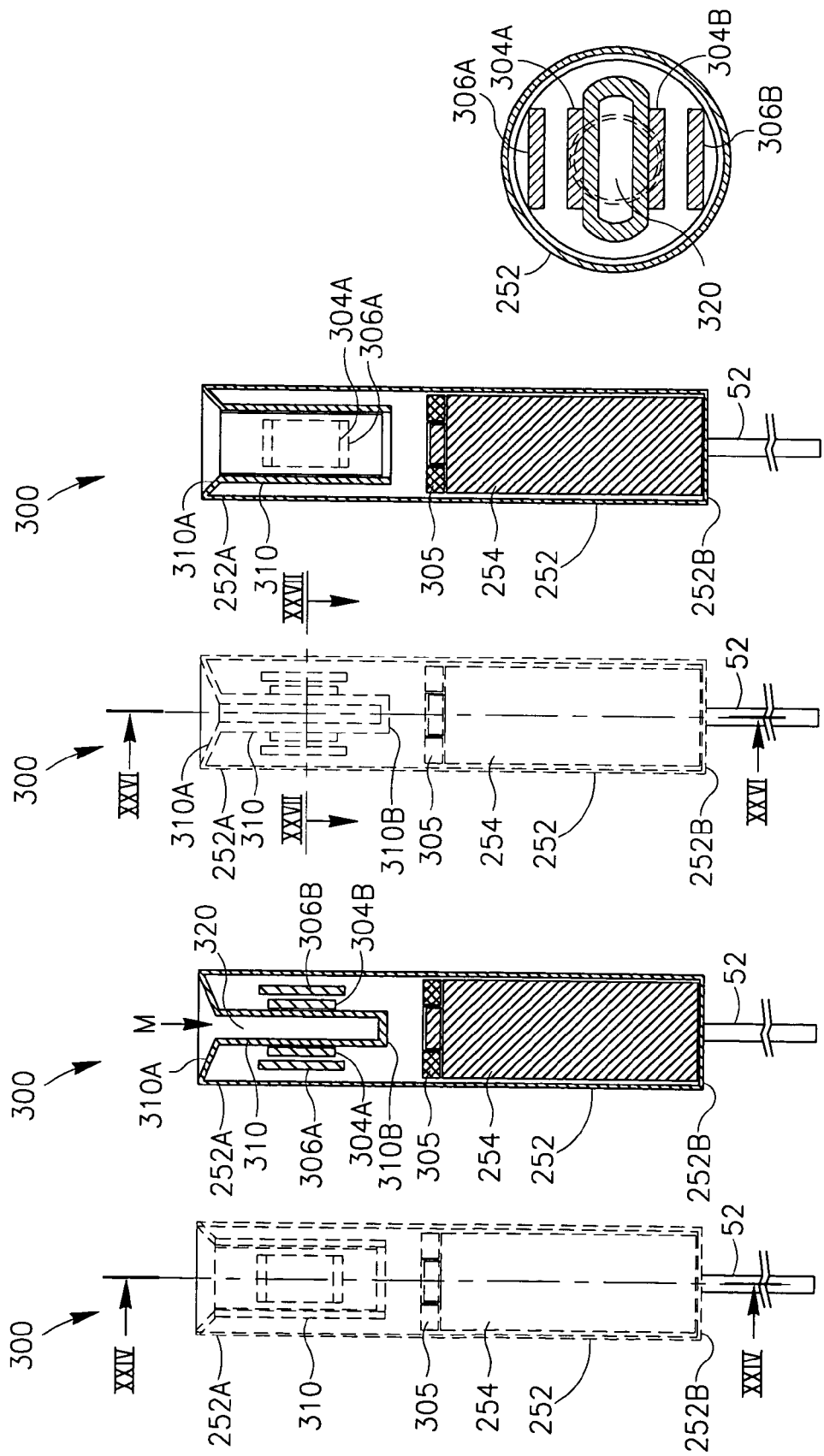

DEVICES, SYSTEMS AND METHODS FOR SHORTENING MENSTRUAL PERIOD DURATION

CROSS-REFERENCE TO RELATED US APPLICATIONS

Related Applications

This Application is a National Phase of PCT Patent Application No. PCT/IL2008/000312 having International filing date of Mar. 9, 2008, which claims the benefit of U.S. Provisional Patent Application Nos. 60/950,054 filed on Jul. 16, 2007 and 60/893,387 filed on Mar. 7, 2007. The contents of the above Applications are all incorporated herein by reference.

FIELD OF THE INVENTION

The present invention relates in general to medical and therapeutic devices and methods and more specifically to devices and methods for applying pressure oscillations to the female vagina and uterus for shortening menstruation duration.

BACKGROUND OF THE INVENTION

Menstruation in women takes place every 28 days on average, and typically lasts between three to nine days (with an average duration of five days). During this period, the uterus sheds 10 to 80 milliliters of bodily substances, with the average being 35 milliliters. Each individual woman experiences a relatively uniform pattern of menstruation, in time and duration, except while experiencing various physiological changes or dysfunctions.

Menses secretion from the uterus originates in the endometrium layer. When the blood supply to this layer is cut off, following a hormonal signal, the cells undergo natural apoptosis, the blood vessels undergo rupture, and the entire endometrium layer is separated from the myometrium layer. The blood does not clot thanks to the enzyme plasmin.

The vasoconstriction process which causes the shedding of the layer is limited predominantly to the first twenty-four hours of menstruation, and the resulting menses fluid accumulated in the uterus starts to be drained slowly through the cervix. Menses fluid is typically a suspension of non-Newtonian fluid, composed of approximately 50% blood, while the other 50% contains other elastic tissue and various bodily particles and fluids. The menses fluid varies in its viscosity, containing tissue particles of 1-20 mm in length (and may be even larger), therefore its flow through the cervix, is restricted and slowed by obstructing the narrow and relatively long uterine cervical lumen and particularly the constrictions in the cervical lumen at the internal os and the external os of the uterine lumen by such tissue particles. Uterine contractions create a pressure gradient between the uterus and the vagina, thus facilitating the shedding process and flow of menses.

The most common female hygienic absorbents are tampons and pads. The goal of these absorbents is to provide women with a solution for absorbing the menstrual secretions. This enables them to continue their daily routine and activities during menstruation.

As used herein the specification and in the claims section that follows, the term "tampon" and the like refer to a wad of substantially absorbent material introduced into a woman's vagina usually to absorb secretions during menstruation.

Absorbent pads and means for conveniently inserting same into the female vagina are disclosed, among others, in U.S. Pat. No. 1,926,900, U.S. Pat. No. 2,024,218. Both of these patents are incorporated by reference for all purposes as if fully set forth herein.

The catamenial device, known by the name of "tampon", which has been improving the lives of millions of women around the world for many years, is primarily designated to eliminate all external pads, belts, etc, and is employed internally in the vagina; however it has no effect on the duration of menstruation. Moreover, from their patenting in 1933 until present, only minor changes were introduced in the materials and shape of tampons and pads. To date, of all the different hygiene devices used by women during menstruation, none eliminates or reduce the discomfort, duration, pain and uneasiness of menstruation.

U.S. Pat. Nos. 5,782,779, and 6,183,428 to Kilgore disclose vibrating tampon apparatus for relieving menstrual pain. The tampon uses an internal mechanical vibrator with the intent to relieve the user from the menstrual pain as well as to facilitate the insertion of the tampon in the case of a dry vagina. The vibrating tampon comprises a tampon with an embedded electric motor, powered by a miniature battery and an ex-centric weight attached to the motor shaft which generates mechanical vibrations of the tampon which are directly transferred to the vaginal canal walls contacting the tampon.

A description of devices generating acoustic waves that can be used to treat patients with cystic fibrosis (CF), bronchitis and other lung dysfunctional diseases, which use acoustic vibrations to stimulate the evacuation of the secreted mucus (sputum), thus facilitating in the lungs clearance, are described in U.S. Pat. No. 5,451,190 to Liardet, U.S. Pat. No. 5,829,429 to Hughes, U.S. Pat. No. 6,631,721, to Salter et al., and in U.S. Pat. No. 7,059,324 to Pelerossi et al., all of which are incorporated by reference in their entirety for all purposes as if fully set forth herein.

U.S. Pat. No. 4,141,360 to Lasswell discloses a menstrual extraction device that causes menstrual extraction to achieve a fast depletion of the menses fluid from the uterus. The device reduces the pressure at the end of the cervix creating suction on the menses fluid. However, this device poses several difficulties and dangers to a potential user, including potentially causing a miscarriage, especially if used incorrectly. Due to possible tissue damage, the application of this device has to be supervised and cannot be self-administered.

Thus, there is a widely recognized need for, and it would be highly advantageous to have a device that can efficiently and safely shorten the duration of the menses flow.

SUMMARY OF THE INVENTION

There is therefore provided a device for shortening menstruation duration. The device includes a pressure oscillations generating unit configured to be inserted into a vagina for applying pressure oscillations to a vaginal chamber defined by part of the device, the walls of the vagina and the cervix of the uterus.

Furthermore, in accordance with an embodiment of the device, the device also includes an absorbent member attached to the pressure oscillations generating unit for absorbing menstrual secretions.

Furthermore, in accordance with an embodiment of the device, the absorbent member is a sleeve like absorbent member attached to the pressure oscillations generating unit and the entire device is disposable.

Furthermore, in accordance with an embodiment of the device, the absorbent member is a sleeve-like absorbent member detachably attachable to the pressure oscillations generating unit. The pressure oscillations generating unit is a reusable unit and the absorbent member is a disposable absorbent member.

Furthermore, in accordance with an embodiment of the device, the device also includes a power source for energizing the pressure oscillations generator unit. The power source is selected from an internal power source disposed within the device and an external power source disposed outside the device and coupled to the pressure oscillations generator unit.

Furthermore, in accordance with an embodiment of the device, the power source is an electrical power source.

Furthermore, in accordance with an embodiment of the device, the power source is selected from a battery, an electrochemical cell, a primary electrochemical cell, a rechargeable electrochemical cell, a super-capacitor, a fuel cell, and any combinations thereof.

Furthermore, in accordance with an embodiment of the device, the pressure oscillations are pressure oscillations having a frequency in the range of 0.1 Hz-10 kHz, more preferably in the range of 1 Hz-100 Hz, and most preferably in the range of 30 Hz-60 Hz.

Furthermore, in accordance with an embodiment of the device, the pressure oscillations generating unit is configured to deliver pressure oscillations having an energy in the range of 0.01-1.0 Watt delivered to the vaginal chamber, but energies larger than 1 Watt may also be used.

Furthermore, in accordance with an embodiment of the device, the pressure oscillations are selected from pressure waves, acoustic waves, periodic acoustic waves, sinusoidal acoustic waves, acoustic shock waves, pulsatile acoustic waves and any combinations thereof.

Furthermore, in accordance with an embodiment of the device, the pressure oscillations are applied to said vaginal chamber intermittently with a duty cycle in the range of 1%-99%.

Furthermore, in accordance with an embodiment of the device, the pressure oscillations generating unit includes at least one movable member coupled to the chamber when the device is disposed in a vagina. The movable member is configured for delivering the pressure oscillations to the chamber.

Furthermore, in accordance with an embodiment of the device, the at least one movable member is a single movable membrane wholly or partially comprised of an electrically conducting material, wherein the membrane is disposed adjacent to an electrically conducting coil included in the pressure oscillations generating unit. The movable membrane is configured to oscillate upon application of a periodically varying current to the coil.

Furthermore, in accordance with an embodiment of the device, the at least one movable member is a movable membrane sealingly attached to a rigid housing of the pressure oscillations generating unit and coupled to a linear motor attached to the housing.

Furthermore, in accordance with an embodiment of the device, the at least one movable member comprises two movable membranes sealingly attached to a rigid housing. Each membrane has a flat electrically conducting coil attached thereto. The device includes two permanent magnets wherein one permanent magnet of the two permanent magnets is attached to the rigid housing adjacent to each membrane of the two membranes.

Furthermore, in accordance with an embodiment of the device, the at least one movable member comprises two movable membranes sealingly attached to a rigid housing. Each membrane has a flat electrically conducting coil attached thereto. The rigid housing also includes two permanent magnets attached thereto. Each permanent magnet is disposed adjacent to a different movable membrane of the two movable membranes.

Furthermore, in accordance with an embodiment of the device, the at least one movable membrane comprises two elastic movable membranes sealingly attached to a rigid housing. Each membrane has a flat permanent magnet attached thereto. The device also includes two electrically conducting coils. A first coil is rigidly attached to the rigid housing adjacent to the permanent magnet of a first membrane, and the second coil is rigidly attached to the rigid housing adjacent to the permanent magnet of a second membrane.

There is also provided a method for shortening the duration of the menstruation period of a female subject. The method includes applying pressure oscillations to a volume of fluid enclosed within the vagina of the female subject, for increasing the rate of flow of menstrual secretions out of the uterus to shorten the duration of the menstruation period.

Furthermore, in accordance with an embodiment of the method, the volume of fluid is contained in a vaginal chamber defined between part of a pressure oscillations generating unit disposed within the vagina, part of the walls of the vagina and the cervix of the female subject.

Furthermore, in accordance with an embodiment of the method, the volume of fluid includes fluids selected from the group consisting of air, menstrual fluid and a combination of air and menstrual fluid.

Furthermore, in accordance with an embodiment of the method, the pressure oscillations generating unit is configured to deliver pressure oscillations having an energy in the range of 0.01-1.0 Watt delivered to the volume of fluid.

Furthermore, in accordance with an embodiment of the method, the pressure oscillations includes pressure oscillations having a frequency in the range of 0.1 Hz-10 kHz, more preferably in the range of 1 Hz-100 Hz, and most preferably in the range of 30 Hz-60 Hz.

Furthermore, in accordance with an embodiment of the method, the pressure oscillations are selected from the group consisting of pressure waves, periodic acoustic waves, sinusoidal acoustic waves, acoustic shock waves, pulsatile acoustic waves and any combinations thereof.

Furthermore, in accordance with an embodiment of the method, the pressure oscillations are applied to the volume of fluid intermittently with a duty cycle in the range of 1%-99%.

There is also provided in accordance with the methods of the present application, a method for shortening menses duration. The method includes the steps of: introducing into a vagina a device including a pressure oscillations generating unit for applying pressure oscillations waves to a vaginal chamber defined by part of said device, the walls of the vagina and the cervix of the uterus, and activating the device to generate pressure oscillations within the vaginal chamber for increasing the rate of flow of menstrual secretions out of the uterus.

Furthermore, in accordance with an embodiment of the method, the step of activating includes providing power to the pressure oscillations generating unit from a power source selected from, an internal power source internally disposed within the device, and an external power source disposed outside the vagina and connected to the pressure oscillations generating unit.

Furthermore, in accordance with an embodiment of the method, the step of activating includes activating the pressure oscillations generating unit by remotely actuating an actuatable switching unit included in the device to provide power from the power source to the pressure oscillations generating unit.

Furthermore, in accordance with an embodiment of the method, the method also includes the step of absorbing menses fluids flowing into the vagina by an absorbent member attached to the pressure oscillations generating unit.

Furthermore, in accordance with an embodiment of the method, the pressure oscillations include pressure oscillations having a frequency in the range of 0.1 Hz-10 kHz, more preferably in the range of 1 Hz-100 Hz, and most preferably in the range of 30 Hz-60 Hz.

Furthermore, in accordance with an embodiment of the method, the pressure oscillations generating unit is configured to deliver pressure oscillations having an energy in the range of 0.01-1.0 Watt delivered to the vaginal chamber.

Furthermore, in accordance with an embodiment of the method, the pressure oscillations are selected from the group including of pressure waves, periodic acoustic waves, sinusoidal acoustic waves, acoustic shock waves, pulsatile acoustic waves and any combinations thereof.

Furthermore, in accordance with an embodiment of the method, the pressure oscillations are applied to the vaginal chamber intermittently with a duty cycle in the range of 1%-99%.

There is further provided in according with an embodiment of the devices of the present application a device for shortening menses duration. The device includes one or more vibration generating units configured to be mechanically coupled to the skin of the body of a menstruating female subject, for directing mechanical vibrations to the region of the uterine cervix of the subject for changing the flow properties of the menses within the uterus of the subject to increase the flow of the menses through the cervix and to shorten the duration of the menstruation period of the female subject. The device also includes a power source for controllably energizing the one or more vibration generating units.

Furthermore, in accordance with an embodiment of the device, the one or more vibration generating units is selected from, one or more piezoelectric transducers, one or more electromechanical transducers, one or more mechanical transducers, and any combinations thereof.

Furthermore, in accordance with an embodiment of the device, the one or more vibration generating units are configured for generating in the tissues of the female subject vibrations selected from pressure waves, shear waves and a combination of pressure waves and shear waves.

Furthermore, in accordance with an embodiment of the device, the one or more vibration generating units are attached to a coupling member selected from a belt-like member, an elastic belt-like member, an adhesive member and any combinations thereof.

There is also provided, in accordance with the present application, a kit for shortening the duration of menstruation period. The kit includes a pressure oscillations generating unit configured to be inserted into a vagina for applying pressure oscillations to a vaginal chamber defined by part of the device, the walls of the vagina and the cervix of the uterus and one or more absorbent members detachably attachable to the pressure oscillations generating unit for absorbing menses.

There is also provided, in accordance with an embodiment of the devices of the present application, a device including a pressure oscillations generating unit configured to be inserted into a vagina for applying pressure oscillations to a vaginal chamber defined by part of the device the walls of the vagina and the cervix of the uterus, and a menses collecting member attached to the pressure oscillations generating unit for collecting menses.

Finally, in accordance with an embodiment of the kit of the present application, the one or more absorbent members are one or more sleeve like absorbent members each absorbent member has a hollow passage formed therein for inserting the pressure oscillations generating unit.

BRIEF DESCRIPTION OF THE DRAWINGS

The invention is herein described, by way of example only, with reference to the accompanying drawings, in which like components are designated by like reference numerals, wherein:

FIG. 7 is a schematic cross sectional side view of the tampon-like device of FIG. 5 taken along the line VII-VII;

FIG. 8 is a schematic partial cross sectional side view of a flat coil and the elastic membrane of the tampon-like device of FIG. 1;

FIG. 9 is a schematic partial cross sectional side view illustrating an internal electronic compartment casing of the tampon-like device of FIG. 7;

FIG. 10 is a schematic top view illustrating the flat coil of the tampon-like device, of FIG. 7;

FIG. 11 is a schematic isometric view illustrating the rigid tube of the tampon-like device, of FIG. 7;

FIG. 12 is a schematic side view illustrating the rigid tube of FIG. 11;

FIG. 13 is a schematic top view illustrating the rigid tube of FIG. 11;

FIG. 16 is a schematic side view illustrating a pressure oscillations generating unit usable in the tampon-like devices of the present application and including a linear motor;

FIG. 17 is a schematic cross sectional view of the pressure oscillations generating unit of FIG. 16 taken along the line XVII-XVII;

FIG. 18 is a schematic cross sectional view illustrating in detail part of the pressure oscillations generating unit of FIG. 17.

FIG. 19 is a schematic side view illustrating a pressure oscillations generating unit usable in the tampon-like devices of the present application and including a cup-like elastic member and two coils, in accordance with another embodiment of the pressure oscillations generating unit of the present application;

FIG. 20 is a schematic cross sectional view of the pressure oscillations generating unit of FIG. 19 taken along the line XX-XX;

FIG. 21 is another schematic side view illustrating the pressure oscillations generating unit of FIG. 19;

FIG. 22 is a schematic cross sectional view illustrating pressure oscillations generating unit of FIG. 21 taken along the line XXII-XXII and also illustrating in detail part of the pressure oscillations generating unit;

FIG. 23 is a schematic side view illustrating a pressure oscillations generating unit usable in the devices of the present application and including a box-like elastic member having two coils and also including two permanent magnets, in accordance with another embodiment of the pressure oscillations generating unit of the present application;

FIG. 24 is a schematic cross sectional view of the pressure oscillations generating unit of FIG. 23 taken along the line XXIV-XXIV;

FIG. 25 is another schematic side view illustrating the pressure oscillations generating unit of FIG. 23;

FIG. 26 is a schematic cross sectional view illustrating the pressure oscillations generating unit of FIG. 23 taken along the line XXVI-XXVI;

FIG. 27 is a schematic top view of the pressure oscillations generating unit of FIG. 26 as seen from the direction represented by the arrow M of FIG. 24;

DETAILED DESCRIPTION OF THE INVENTION

Notation Used Throughout

Figure 1:
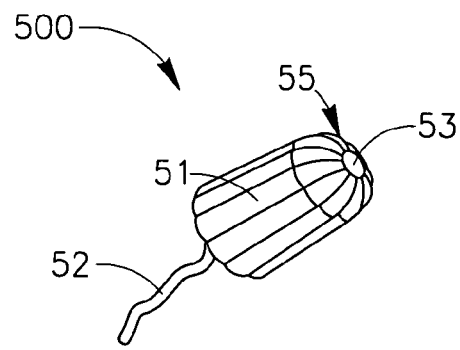
FIG. 1 is a schematic perspective view of tampon-like device, in accordance with an embodiment of the menstruation period shortening devices of the present application.

The following notation is used throughout this document.

| Term | Definition |
| --- | --- |
| AC | Alternating current |
| cm | Centimeter |
| DC | Direct current |
| Hz | Hertz |
| kHz | Kilohertz |
| ml | Milliliter |
| mm | Millimeter |
| Mpa | MegaPascal |
| mWhr | Milliwatt hour |
| PCB | Printed circuit board |
| PET | Polyethylene Terephtalate |
| PVC | Polyvinyl Chloride |
| W | Watt |

The devices, systems and methods disclosed in the present application are medical and therapeutic devices and methods that apply vibrations to non-Newtonian fluids, which facilitate and induce streaming behavior on various fluids within various cavities and lumens of the human body.

One of the therapeutic effects according to the present invention is the acceleration of the menses flow leading to the shortening of the duration of the menstruation period.

Shear and vibrational viscosity thinning are both well-known physical phenomena that take place when non-Newtonian suspension type fluids are subjected to oscillatory waves. The two main used forms of waves are pressure waves and shear waves. Cyclic energy applied to a suspension type fluid causes the breakup of flow obstructing aggregations of the different elements in the fluid and possible streamlined re-aggregation. The result of this behavior is a reduction of the effective dynamic viscosity of the fluid. Thus, in essence the waves applied to the fluid cause a significant reduction in the fluid's resistance, therefore, the non-Newtonian fluid can flow significantly faster than without the applied energy.

The devices, systems and methods disclosed herein use a powered device for directly assisting women in shortening the menstrual flow period. The device may be self administered in a simple and safe manner to spare its user lengthy menstrual flow. Such devices maybe convenient for the user to wear and do not impede the user's mobility.

The duration of draining of menses fluid is shortened by means of reducing its effective viscosity. This is achieved by acoustically vibrating the menses fluid and the adjacent tissue, which by nature has the flow qualities of non-Newtonian fluids, such that it achieves flow qualities of, or similar to, newtonian fluid with reduced effective dynamic viscosity.

As used herein the specification and in the claims section that follows, the term "Newtonian fluid" and the like refer to a fluid whose stress at each point is linearly proportional to its strain rate at that point.

Some of the devices described herein may be pressure oscillations generating unit remotely (electronically, magnetically or otherwise) activated prior to their insertion into the vagina; the activation is by means of a magnetic switch or any other suitably remotely actuatable switching unit or switching mechanism, as is known in the art. This is done in order to ensure the absolute sealing of the electronic compartment from the exterior environment. The device can be inserted into the vaginal cavity through the use of a conventional tampon cardboard applicator.

In another embodiment of the present invention, oscillators or vibrating units are worn externally and are fitted on a belt placed around the abdomen, or otherwise attached to the abdominal region of the body (such as, but not limited to by the use of adhesive pads, or the like). The vibrating units are aimed towards the center of the abdomen where the uterus and/or cervix is located, where geometric focusing and constructive interference result with large oscillations. The power unit may also attached to the belt. In this embodiment, the vibrating units can generate two different types of waves. One type is the regular pressure wave at a frequency in the range of 1 Hz to 10 kHz, with an oscillator membrane maximum amplitude which is typically 0.1 mm to 2 mm. The generating mechanism in the vibration generating units can be a simple ex-centric motors or any other suitable other oscillating or vibration generating unit and/or mechanism or device, as is known in the art. The second type of wave is the shear waves. The vibration generating mechanism for that type of wave is a shear wave generating unit at similar amplitudes and frequencies as the pressure emitters.

As used herein the specification and in the claims section that follows, the term "pressure wave" and the like refer to a longitudinal wave for which the particle displacement is parallel to the direction of wave propagation.

As used herein the specification and in the claims section that follows, the term "shear waves" and the like refer to transverse waves in which the particle displacement is perpendicular to the direction of wave propagation.

The present invention may be better understood with reference to the following scientific papers:

1. Boris N Ouriev, and Naum B Uriev, *Influence of vibration on structure-rheological properties of a highly concentrated suspension*, Meas. Sci. Technol. 16 1691-1700, (2005);
2. Boris Ouriev, *Rheology and Rheometry of Aluminum alloys: influence of shear and vibration on aluminum flow properties*, Solid State Phenomena Vols. 116-117 pp. 558-564 (2006);
3. Youbing Li, Kaizhi Shen, and Jie Zhan, *Improving Rheological Property of Polymer Melt Via Low Frequency Melt Vibration*" Journal of Applied Polymer Science, Vol. 102, 5292-5296 (2006);
4. J. Bear, *Dynamics of Fluids in Porous Media*, sec. 5.10. American Elsevier Pub. Co., (1972);
5. Yingzi Chen, Huilin Li, *Effect of Ultrasound on the Viscoelasticity*, The State Key Laboratory of Polymer Materials Engineering, Polymer Research Institute of Sichuan University, Chengdu 610065, People's Republic of China, received 13 Nov. 2003; accepted 13 Apr. 2004, DOI 10.1002/app.20831, published online in Wiley Inter-Science (www.interscience.wiley.com);
6. N B Uriev, and I V Kuchin, *Modelling of the dynamic state of disperse systems*, #2006 Russian Academy of Sciences and Turpion Ltd Russian Chemical Reviews 75 (1) 31±55 (2006);
7. Y. J. Liu, *Rheological equation for polymer melt under the action of vibration*, Plastics, Rubbers and Composites VOL 34 NO 2 (2005);
8. T A Scherer, J Barandun, E Martinez, A Wanner and E M Rubin, *Effect of high-frequency oral airway and chest wall oscillation and conventional chest physical therapy on expectoration in patients with stable cystic fibrosis*, CHEST/113 4 April, 1019 (1998);
9. FDA Approval, *High-Frequency Ventilator*, PMA Number P890057/S14, Sep. 24, 2001;

All of the above cited eight papers are incorporated herein by reference in their entirety for all purposes as if fully set forth herein.

In the specific applications adapted for shortening the duration of menses, the devices, systems and methods disclosed herein may use pressure oscillations, and/or acoustic waves and/or shock waves, and/or shear waves to vibrate the vaginal cavity, uterus, the uterus cavity, and the menses fluids.

The devices, systems and methods disclosed herein use and apply a physical principle called 'streaming'. The waves of the device cause streaming of the menses fluids. The streaming effect of suspension, non-Newtonian fluids is well known and applied in different industrial applications. Ref [1] demonstrates the effect of vibrations on chocolate and finds the range of amplitudes and frequencies in which the non-Newtonian fluid flows as a Newtonian fluid. Ref [2] compares the changes in the rheological properties of aluminum suspension flow with and without vibrations. Ref [3] shows the effect of vibrations during the manufacturing extrusion process of a polymer. In the above mentioned scientific literature, the vibrations are used to lower the effective viscosity of the suspension liquid.

The reduced effective viscosity is the combined result of two important physical processes taking place in the flow of a suspension fluid. First, the effect of vibration is to phase separate the medium and allow the aggregation of the suspension component. Once aggregation takes place, the fluid part of the medium can flow more easily as it is on average further away from obstructions. General models of a flow in porous media give, for example, an effective dynamic viscosity which is inversely proportional to the squared size of the structures (i.e., aggregates in the present case) (e.g., Ref [4]). The effect is generally temporary and completely reversible. It stops once the vibrations cease. Note however, that the effect can still be present several seconds later, due to a possible memory effect. According to the present invention, the generated pressure oscillations (and/or acoustic waves and/or shock waves) waves for applying the streaming effect in menses vibrate the tissue as well as the menses fluid and can be optimized for the reduction of the effective viscosity of menses fluid.

Figure 2:
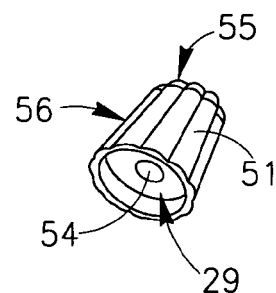
FIG. 2 is a schematic perspective view of a compressed cotton sleeve of the tampon-like device, of FIG. 1.
Figure 3:
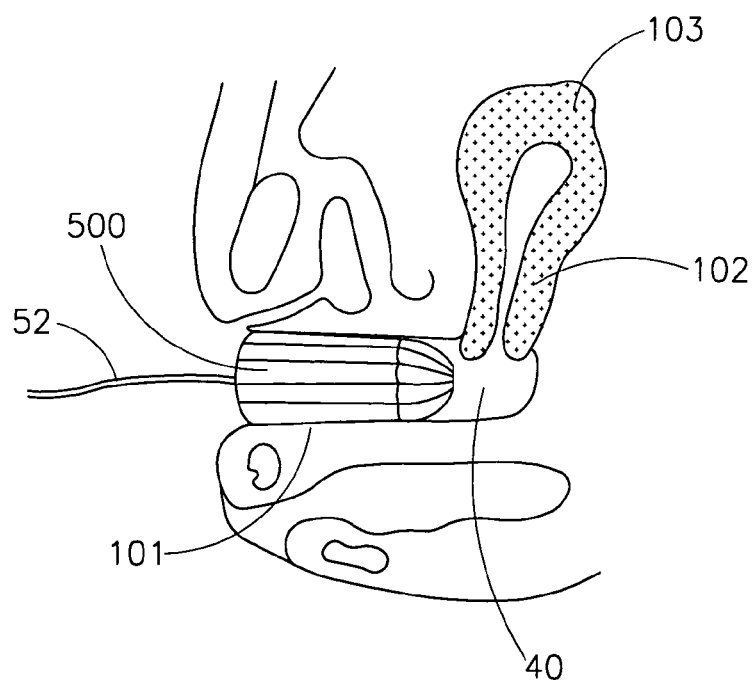
FIG. 3 is a schematic side view of the tampon-like device, of FIG. 1, in position in a vagina.
Figure 4:
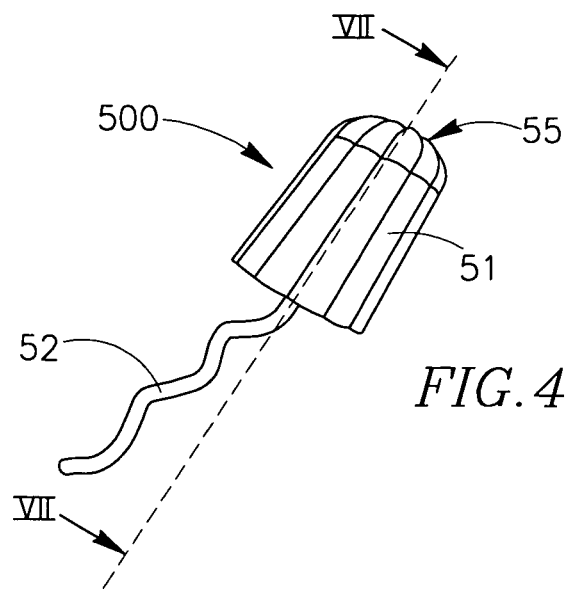
FIG. 4 is a schematic side view of the tampon-like device, according to the present invention.
Figure 5:
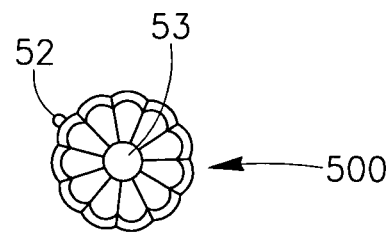
FIG. 5 is a schematic illustration in view from the edge of the insertion side of the tampon-like device of FIG. 1.
Figure 6:
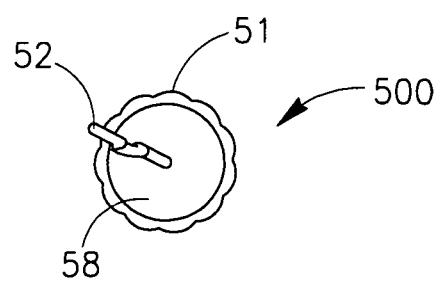
FIG. 6 is a schematic illustration in view from the bottom of the tampon-like device, of FIG. 1.

Reference is now made to FIGS. 1-13. FIG. 1 is a schematic perspective view of a tampon-like device, in accordance with an embodiment of the menstruation period duration shortening devices of the present application. FIG. 2 is a schematic perspective view of a compressed cotton sleeve of the tampon-like device, of FIG. 1. FIG. 3 is a schematic side view of the tampon-like device of FIG. 1, disposed in position in a vagina. FIG. 4 is another schematic side view of the tampon-like device of FIG. 1. FIG. 5 is a schematic top view of one end of the tampon-like device of FIG. 4 viewed from the edge of the insertion side of the tampon-like device of FIG. 1. FIG. 6 is a schematic bottom view of the tampon-like device of FIG. 4 illustrating the bottom part of the tampon-like device. FIG. 7 is a schematic cross sectional side view of the tampon-like device of FIG. 5 taken along the line VII-VII. FIG. 8 is a schematic partial cross sectional side view of a flat coil and an elastic membrane of the tampon-like device of FIG. 1. FIG. 9 is a schematic partial cross sectional side view illustrating an internal electronic compartment casing of the tampon-like device of FIG. 7. FIG. 10 is a schematic top view illustrating the flat coil of the tampon-like device of FIG. 7. FIG. 11 is a schematic isometric view illustrating the rigid tube of the tampon-like device of FIG. 7. FIG. 12 is a schematic side view illustrating the rigid tube of FIG. 11, and FIG. 13 is a schematic top view illustrating the rigid tube of FIG. 11.

Turning to FIG. 1, a tampon-like device 500, in accordance with an embodiment of the active devices of the present application, is illustrated. FIG. 1 illustrates three external components of the tampon-like device 500. A compressed cotton sleeve 51, which is an absorbent member constructed and operative like the absorbent part of a standard tampon, a pulling cord 52 attached to the battery compartment 58 of FIG. 7 (or alternatively to the cotton sleeve 51), which may be used for pulling and removing tampon-like device 500 from the vagina, and an elastic membrane 53, which may be operated for producing pressure oscillations and/or acoustic waves and/or shock waves as disclosed in detail hereinafter.

The insertion side end 55 of the tampon-like device 500 has rounded corners in order to facilitate insertion to the vaginal cavity. The exterior surface 56 of the compressed cotton sleeve 51 can have a multi-lobed shape having small circular curves which resembles a top view of a flower, as shown in the present figure, but any other suitable shapes may be used.

The purpose of this shape is to increase the outer surface of the absorbent part, compressed cotton sleeve 51, or any other material which could be used for absorption, thus increasing the absorbance capability of the highly viscous substances that are part of the menses fluid and do not penetrate compressed cotton.

For the purpose of the following descriptions, we will define the side on which the membrane 53 is disposed in the tampon-like device 500, as shown in the illustration, as the insertion side (or top side), and the opposite side, to which the pulling cord 52 is attached, as the bottom side of the tampon 500.

Turning to FIG. 2, the compressed cotton sleeve 51 of the tampon-like device 500, is viewed from the bottom side. A recess 29 is formed within the bottom part of the compressed cotton sleeve 51. The recess 29 is used to house a battery compartment (not shown in FIG. 2), as described in detail hereinbelow with respect to FIG. 7. At the center of the cotton sleeve 51, there is a longitudinal generally cylindrical passage 54 longitudinally passing through the cotton sleeve 51. The passage 54 which is configured to contain a rigid tube, (the rigid tube is not shown in FIG. 2 for the sake of clarity of illustration, but is described in FIG. 7 hereinafter). The passage 54 has a first end opening at the side of the recess 29, and the other end opening at the top side (the insertion side as defined hereinafter) of the tampon 500.

Turning to FIG. 3, the tampon-like device 500 is illustrated disposed in a vagina 101. The illustration also shows the cervix 102, and the uterus 103. When the tampon-like device 500 is placed within the vagina 101, as shown in FIG. 3, an enclosed vaginal chamber 40 is formed and defined between the walls of the vagina 101, the cervix 102 and part of the insertion side 55 of the tampon 500.

Turning now to FIG. 4, the tampon-like device 500 includes the compressed cotton sleeve 51, for absorbing menses secretions, as is well known in the art. The tampon-like device 500 also includes a pulling cord 52, which may be used for pulling out and removing the tampon-like device 500 from the vagina 101. The insertion side end 55 of the tampon-like device 500 is shown. The illustration also shows the pulling cord 52, and the elastic membrane 53.

Turning to FIG. 6, the bottom end of the tampon-like device 500, of FIG. 4 is illustrated. The illustration also shows the pulling cord 52 attached to a battery compartment 58 disposed within the recess 29 (see FIG. 2) of the compressed cotton sleeve 51.

Turning to FIG. 7, a cylindrical tube 57 is disposed within the passage 54 formed within the cotton sleeve 51. The tube 57 may be made from a preferably biocompatible suitable plastic or polymer based material or any other suitable rigid material known in the art, such as, but not limited to polypropylene, polyethylene terephtalate (PET), polyethylene and the like. The tube 57 is sealingly attached at a first end 57A thereof to a battery compartment 58. The battery compartment 58 may be any type of sealable housing made from a suitable polymer base material or any other suitable structural material known in the art for sealingly holding a battery 59 or other suitable power source therewithin.

A flat electrically isolated, electrically conducting coil 60 (best seen in FIGS. 8 and 10) is attached to the end 57B of the tube 57. The coil 60 may be a planar spirally formed coil made from any suitable electrically conducting material such as but not limited to, copper, aluminum, an electrically conducting polymer and the like. The coil 60 may be electrically isolated by a suitable thin isolating material (not shown in the figures for the sake of clarity of illustration), such as Teflon®, or any other suitable isolating material such as an electrically isolating varnish, an elastomer, plastic, and the like.

The circumferential end 60C of the coil 60 is suitably sealingly attached (by a suitable sealing glue, or by any other attachment method known in the art) to the (open) end 57B of the tube 57. An elastic membrane 53 is suitably circumferentially and sealingly attached to the part 60C of the coil 60 such that the electronic compartment 47 formed within the tube 57 is a sealed compartment. The elastic membrane 53 is a thin flat membrane which is made from an electrically conducting material. For example, the elastic membrane may be a thin elastic foil made from aluminum, copper or any other suitable electrically conducting elastic material, such as but not limited to an elastic electrically conducting polymer.

Preferably, the elastic membrane 53 is an elastic, thin, electrically isolating membrane made from Mylar®, Polypropylene, or any other suitable plastic or polymer or the like and is coated or painted with a layer of electrically conducting material such as a metal or electrically conducting polymer or the like (The electrically conducting layer is not shown in the Figures). In this case, the electrically conducting layer is coated or painted or deposited only on the side 53B of the membrane 53 facing the coil 60 and not on the side 53A of the membrane 53 which faces the external side of the tampon 500. For example, the elastic membrane 53 may be a disc-like shaped piece of Mylar® Aluminized on one side only, as is known in the art.

It is noted that all of the internal electronic and mechanical parts disposed within the sealed compartment 47 and within the battery compartment 58 are sealingly protected from the fluids with which the tampon-like device 500 may come into contact.

The electronics compartment 47 includes electronic circuitry, such as the printed circuit board (PCB) 45. The PCB 45 includes all the circuitry necessary for forming a frequency generating unit configured for generating an oscillatory or periodically varying electrical current as is described in detail hereinafter. The theory and practice of electronic circuits for generating oscillating currents is well known in the art, is not the subject matter of the present invention and is not described in detail, hereinafter.

Briefly, any suitable oscillating and/or periodically varying current generating unit or circuitry known in the art may be implemented on the PCB 45 or other circuitry disposed in the sealed electronics compartment 47, such as a simple RC circuit(s), RLC circuit(s), or any other oscillating circuit known in the art that receives direct current as input and outputs an oscillating current (or oscillating voltage) having one or more frequencies or a periodically varying current. It noted that the PCB 45 may include analog circuit(s) and/or components, and/or Digital circuits and/or components and/or any combinations of analog and digital circuits and/or components. The PCB 45 may also include any suitable combination of multiple oscillator circuits which may be used to generate current oscillations having different frequencies or periodic current waveforms having different frequencies and wave-shapes.

Turning to FIG. 8, the coil 60 has coil terminals 60A and 60B. The coil terminals 60A and 60B of the coil 60 are electrically connected to two isolated electrical wires 43A and 43B (best seen in FIG. 7) which are also electrically connected to the PCB 45 for providing the oscillating current and/or a periodically varying current to the coil 60.

When a periodically varying current (or an oscillating current, such as, but not limited to a sinusoidal current) is applied to the coil 60, the currents flowing through the coil 60 induces eddy currents in the metal forming the elastic membrane 53 or deposited in a layer thereupon (depending on the type of membrane being used). These induced eddy currents cause a periodically varying force pushing the elastic membrane away from the surface of the coil 60. As the elastic membrane 53 is attached only partially to the coil 60 only at the narrow circumferential part 60C as disclosed hereinabove, most of the surface 53B of the elastic membrane 53 is not permanently attached to the surface of the coil 60 and may move away from and/or towards the surface of the coil 60 when a suitable force is applied thereto.

Thus, as long as the oscillating and/or periodically varying currents are applied to the coil 60, the part of the elastic membrane 53 which is not attached to the circumference 60C of the coil 60 will mechanically oscillate along the general direction of the longitudinal axis of the tampon 500 represented by the double headed arrow 35. When the tampon 500 is disposed in the vagina 101 as illustrated in FIG. 3, and the power is switched on to energize the circuitry of PCB 45, the oscillations and/or periodic movement of the elastic membrane 53 push the air adjacent to the side 53A of the elastic membrane 53 generating pressure oscillations and/or acoustic waves and/or shock waves (depending, inter alia, on the particular waveform of the periodically varying currents flowing through the coil 60) in the vaginal chamber 40.

The advantage of applying pressure oscillations (and/or s and/or shock waves) to the vaginal chamber 40 is that a large portion of the oscillation energy is used to generate a varying pressure gradient across the uterine cervical canal connecting the internal space of the uterus 103 with the vaginal air chamber 40. The inventor of the devices disclosed herein surprisingly and unexpectedly found that the application of such pressure oscillations and/or acoustic waves and/or shockwaves to the vaginal air chamber 40 significantly assists and accelerates the flow of menses secretions from the uterus 103 through the cervical canal leading to a very substantial shortening of the menstrual period duration, as disclosed in detail in the experiments described hereinafter.

The PCB 45 may also include a remotely actuatable switching unit, such as a magnetic field actuatable switch that may control the flow of current from the power source (such as, for example, the battery 59 of FIG. 7) to the oscillating and/or periodic current generating circuitry included in the PCB 45. Thus, when the tampon 500 is in storage or not being used, the switch is (by default) in the "off" state and no power is supplied to the PCB 45. The switch (not shown) may then be activated (turned to the "on" state) by the user, (for example by placing a magnet close to the tampon 500 to turn on the switch and energize the circuitry of the PCB 45).

When the switch is turned on, power is supplied to the PCB 45 and the circuitry of the PCB 45 outputs an oscillating and/or periodically varying current through the wires 43A and 43B to the coil 60.

It is noted that the tube 57 functions as a rigid support holding the coil 60 and the elastic membrane 53 attached to the circumference 60C of the coil 60. The tube 57 also seals the internal electronics compartment 47 formed within the tube 57 from any liquids present in the exterior environment. The battery compartment 58 similarly functions to hermetically isolate and seal the battery 59 from the external environment, in order to prevent any electrical discharge to the body.

Turning to FIG. 9, the tube 57 and the battery compartment 58 are attached together forming an internal electronic compartment casing 61 of the tampon-like device 500. The cross-section illustrated in FIG. 9 is taken along the line VII-VII of FIG. 4. The internal electronic compartment casing 61 includes the rigid tube 57, and the battery compartment 58. All the electronic components of the tampon-like device 500 are disposed within the internal electronic compartment casing 61 which provides sealing to the electronic compartment from the external environment.

Turning to FIG. 10, the flat coil 60 of the tampon-like device 500 is illustrated viewed from the top side. It is noted that the details of the flat coil 60 as shown in this exemplary-non-limiting illustration, such as the number of turns, are not meant to be limiting in any way and other coils having a different number of turns and cross-sectional shape may also be used.

In another embodiment of the devices of the present application, the pressure oscillations and/or acoustic waves and/or shock waves may be generated by using a small motor attached to a suitable piston. In each case the frequency of the vibrations may be between 1 Hz and 10 kHz, and the amplitude of the vibrations may be between 0.1 mm to 2 mm.

Usable pressure oscillations may be as follows:

a. a symmetrical subsonic wave in the range of 10 Hz to 1 kHz.

b. a superposition of the two waves into a 1 Hz saw-tooth shaped wave where a higher wave of the range of 10 Hz to 1 kHz is added to its second part.

It is noted that the oscillation frequency range, frequency combinations, and vibration amplitudes mentioned hereinabove while found to be practical, are not intended to limit the scope of the oscillation parameters usable with the various embodiments of the present invention. Other different ranges of oscillation frequency or frequency combinations lower than 1 Hz or higher than 10 kHz may also be used in the devices of the present invention. For example the oscillation frequency may be in the range of 0.1 Hz-10 kHz, more preferably in the range of 1 Hz-100 Hz, and most preferably in the range of 30 Hz-60 Hz. However, other different oscillation frequencies or frequency combinations may also be used.

Similarly, vibration amplitudes lower than 0.1 mm or higher than 2 mm may be used, depending, inter alia, on the particular type, structure and dimensions of the pressure oscillation generating unit being used.

The tampon-like device 500 may be activated by using a small magnet not shown in the illustrations to activate a magnetically actuatable switch (not shown) included in the device 500. Once the tampon-like device 500 is ready to be used, the oscillator is activated by the exterior magnet. Once the oscillator is in operative mode its action will be stopped only upon the depletion of the batteries. The oscillator can be active between 20 minutes to one hour.

However, it is noted that in other embodiments of the devices of the present application the power source may be switched on and off at the user's discretion, such as, for example in devices having an external switchable power source (see, for example the power source 358 of the system 380 of FIG. 33 hereinafter). When such a larger external power source is being used, the duration of activation of the oscillator may be greatly extended as the batteries or other power sources used may have much greater capacity.

Additionally, even in devices having a small internal capacity, the duration of oscillator activation may be extended beyond one hour by activating the oscillator of the device intermittently (in a pulsatile manner) with a duty cycle between smaller than 100% (such as for example with a duty cycle in the range of 1%-99%).

Turning to FIGS. 11, 12 and 13, the tube 57 of the tampon-like device 500, are illustrated in perspective view, side view and top view, respectively.

It is noted that the exemplary pressure oscillations generating unit disclosed hereinabove and illustrated in FIGS. 7-13 is not limited to the particular embodiment described with respect to FIGS. 7-13.

Figure 14:
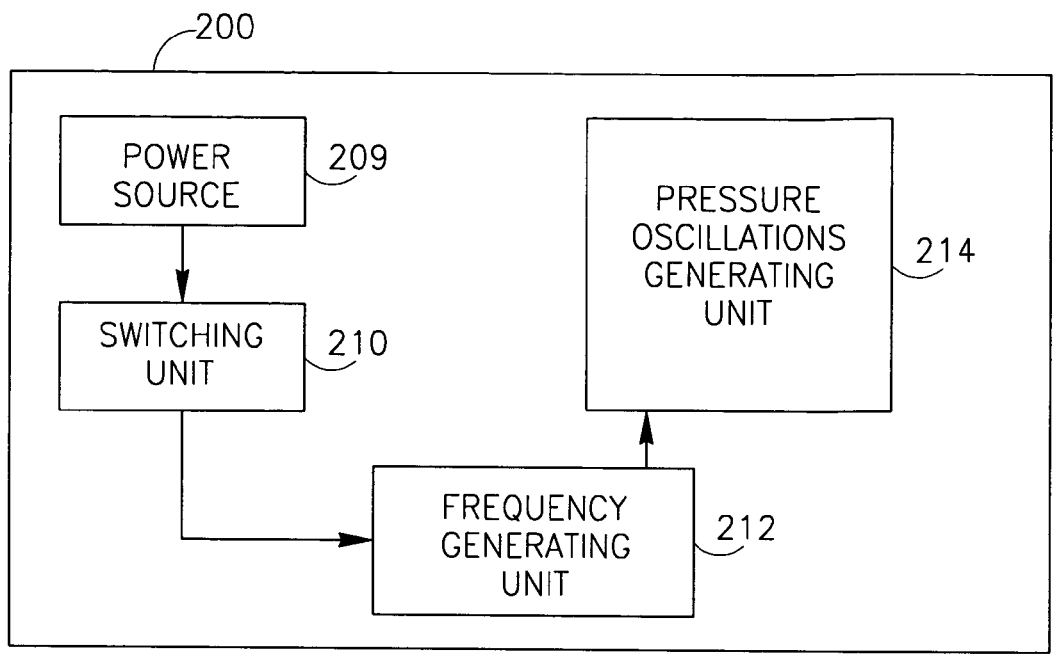
FIG. 14 is a schematic block diagram illustrating some of the components of a menstruation period duration shortening device having an internal power source, in accordance with an embodiment of the devices of the present application.
Figure 15:
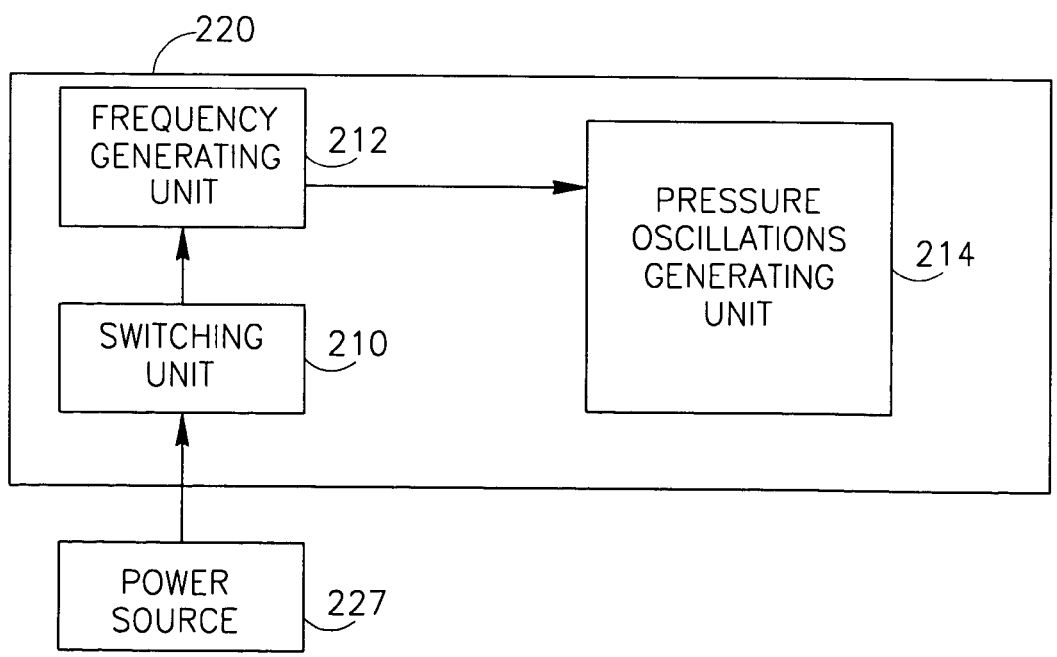
FIG. 15 is a schematic block diagram illustrating some of the components of a menstruation period duration shortening device having an external power source, in accordance with another embodiment of the devices of the present application.

Reference is now made to FIGS. 14-15 which are schematic block diagrams illustrating two different embodiments of the tampon-like device of the present application. FIG. 14 is a schematic block diagram illustrating some of the components of a menstruation period duration shortening device having an internal power source, in accordance with an embodiment of the devices of the present application, and FIG. 15 is a schematic block diagram illustrating some of the components of a menstruation period duration shortening device having an external power source, in accordance with another embodiment of the devices of present application;

Turning to FIG. 14, the device 200 includes a frequency generating circuit 212 which may be any type of electrical or electronic circuit configured for providing oscillating electrical current (or an oscillating voltage) at the frequency or frequencies disclosed herein. The frequency generating circuit 212 is connected to an electrical power source 209 through a controllable switching unit 210, and may receive electrical power from the Power source 209 when the switching unit 210 is actuated to the "ON" state (which may be performed remotely if the switching unit is of the remotely actuatable type as disclosed in detail herein).

The electrical power source 209 is an internal power source disposed within the device 200 and may be any suitable compact electrical power source known in the art, such as but not limited to, a battery, an electrochemical cell, a primary electrochemical cell; a rechargeable electrochemical cell, a super-capacitor, a fuel cell and any combinations thereof. The Frequency generating unit 212 may be any type of electrical circuit for generating time varying electrical signals and or periodically oscillating electrical signals, as disclosed in detail hereinabove.

The frequency generating unit 212 is also connected to a pressure oscillations generating unit 214 by suitable electrical conductors (not shown in detail in FIG. 14). When the power is switched on, the frequency generating unit 212 supplies appropriate oscillating or periodically varying electrical signals to the pressure oscillations generating unit 214 which generates pressure oscillations and/or acoustic waves and/or shock waves within the vagina 101 as disclosed in detail hereinabove.

Turning to FIG. 15, the device 220 includes the frequency generating circuit 212, controllable switching unit 210, and the pressure oscillations generating unit 214 disclosed hereinabove. The device 220 includes an external power source 227. The external power source 227 is a power source disposed outside the device 220 and may be any type of electrical power source known in the art such as but not limited to a DC power source an AC current source (with or without a transformer), a battery, an electrochemical cell, a primary electrochemical cell, a rechargeable electrochemical cell, a supercapacitor, a fuel cell and any combinations thereof. The external power source 227 may be suitably connected to the switching unit 210 (as shown in FIG. 15) but may also (optionally) be a switchable external power source directly connected to the frequency generating unit 212. in the latter case the internal switching unit 210 is replaced by a switching unit (not shown) included in the external switchable power source.

Reference is now made to FIGS. 16-18. FIG. 16 is a schematic side view illustrating an pressure oscillations generating unit usable in the devices of the present application and including a linear motor. FIG. 17 is a schematic cross sectional view of the pressure oscillations generating unit of FIG. 16 taken along the line XVII-XVII. FIG. 18 is a schematic cross sectional view illustrating in detail part of the pressure oscillations generating unit of FIG. 17.

The pressure oscillations generating unit 250 includes a housing 252 which is a cylindrical housing having an opening at one end 252A. The housing 252 may be made from any suitable biocompatible rigid structural material such as, plastic or a polymer based rigid material or any other suitable rigid material known in the art, such as, but not limited to polypropylene, polyethylene terephtalate (PET), polyethylene and the like. A power source such as a battery 254 is disposed within the housing 252. The power source may be any suitable type of compact power source as disclosed in detail hereinabove. In the exemplary embodiment illustrated in FIGS. 16-17, the battery 254 is a standard N type battery, but any other type of battery may be used. The pressure oscillations generating unit 250 also includes a linear motor 256 having a motor shaft 257 which is movable along the directions indicated by the double headed arrow 258. The shaft 258 is mechanically coupled to a movable member 260. The movable member includes a rigid conical portion 260A which is sealingly attached to the opening at the end 252A of the housing 252 (such as, for example by suitable gluing or welding or any other method known in the art). The movable member 260 also includes a preferably rigid bottom portion 260B to which the motor shaft 257 is attached. The movable member 260 also includes a corrugated (accordion-like) flexible portion 260C which may elastically be elongated and shortened in the direction of movement of the motor shaft 257.

A printed circuit board (PCB) 245 is disposed in the housing 252. The PCB 245 is suitably electrically connected to the battery 254 to receive electrical power from the battery 254 (the electrical connections are not shown for the sake of clarity of illustration). The PCB 245 may include a remotely actuatable switch (such as, for example the switching unit 210 of FIG. 14) that may be implemented as a magnetically actuated switch as disclosed hereinabove, however, any other type of remotely actuatable switching device may be used, as is known in the art. The PCB 245 also includes a controller (not shown in detail) which controls the movement of the shaft 257 of the linear motor. The controller is configured for moving the shaft 257 to push or pull the rigid portion 260C such that the corrugated flexible portion 260C is shortened and extended periodically. The movements of the motor shaft 257 may thus be controlled by the controller included in the PCB 245 such that the movable member 260 may generate any desired type of pressure oscillations, and/or acoustic waves, and/or shock waves, and/or pressure waves of a desired frequency or frequencies as disclosed in detail hereinabove and hereinafter. The PCB 245 is electrically connected to the linear motor 256 (the electrical connections are not shown in FIG. 17 for the sake of clarity of illustration) for providing suitable electrical signals to the motor 256 for controlling the movements of the shaft 257 and the frequency and wave shape and (optionally) the duty cycle of the pressure oscillations generated by the moving member 260.

A pulling cord 52 (see also FIG. 7) may be attached to the bottom end 252B of the housing 252 for assisting the removal of the pressure oscillations generating unit from the vagina 101 as disclosed hereinabove. The pressure oscillations generating unit 250 may be inserted into the vagina 101 (see FIG. 3) with the end 252A inserted first into the vagina 101 until a vaginal chamber is defined between the end 252A, the walls of the vagina 101 and the cervix 102. When the pressure oscillations generating unit 250 is activated, pressure oscillations and/or acoustic waves and/or shock waves are generated within the vaginal chamber as disclosed in detail hereinabove to effect the change of flow rate of menses effectively shortening the duration of the menstruation period.

Reference is now made to FIGS. 19-22. FIG. 19 is a schematic side view illustrating a pressure oscillations generating unit usable in the devices of the present application and including a cup-like elastic member and two coils, in accordance with another embodiment of the pressure oscillations generating unit of the present application. FIG. 20 is a schematic cross sectional view of the pressure oscillations generating unit of FIG. 19 taken along the line XX-XX. FIG. 21 is another schematic side view illustrating the pressure oscillations generating unit of FIG. 19. FIG. 22 is a schematic cross sectional view illustrating the pressure oscillations generating unit of FIG. 21 taken along the line XXII-XXII and also illustrating in detail part of the pressure oscillations generating unit.

The pressure oscillations generating unit 270 includes a housing 252 which is a cylindrical housing having an opening at one end 252A. The housing 252 may be made from any suitable biocompatible rigid structural material such as, plastic or a polymer based rigid material or any other suitable rigid material known in the art, such as, but not limited to polypropylene, polyethylene terephtalate (PET), polyethylene and the like. A power source such as a battery 254 is disposed within the housing 252. The power source may be any suitable type of compact power source as disclosed in detail hereinabove. In the exemplary embodiment illustrated in FIGS. 19-22, the battery 254 is a standard N type battery, but any other type of battery may be used.

The pressure oscillations generating unit 270 also includes a cup-like movable member 280. The movable member 280 is shaped like a flaring cup, but other suitable shapes may also be used. The movable member 280 may be a thin elastic membrane made from a suitable biocompatible elastic material, such as but not limited to Milar® or any other type of elastic biocompatible plastic or polymer based material known in the art or the like. The open end 280A of the movable member 280 is sealingly attached to the opening at the end 252A of the housing 252 (such as, for example by suitable gluing or welding or any other method of sealably attaching method known in the art).

Two flat thin electrically conducting plates 272A and 272B are attached to or glued on opposite sides of the movable member 280. The plates 272A and 272B are rectangular in shape but may also be shaped as elliptical plates or as plates having other suitable shapes. The plates 272A and 272B may be made from any suitable electrically conducting material such as but not limited to a metal, aluminum, copper, silver, an electrically conducting polymer and the like. Two rectangular coils 274A and 274B are rigidly attached to the housing 252 such that the coil 274A is adjacent to the plate 272A and the coil 274B is adjacent to the plate 272B. The coils 274A and 274B are preferably planar coils, but other types of non-planar coils may also be used. The coils 274A and 274B are preferably wound from thin insulated electrically conducting wires (not shown in detail), but may also be planar or non-planar coils printed on a thin printed circuit board (PCB) as is known in the art, or any other type of suitable coils). It is noted that the windings of the electrical wires or conductors included in the coils 274A and 274B are not shown in detail in FIGS. 19-22 for the sake of clarity of illustration.

Preferably, the surface of the plates 272A and 272B which face the coils 274A and 274B, respectively, are electrically isolated by a thin layer of non-electrically conducting material or paint (not shown), to ensure that the conducting material of the plates 272A and 272B does not electrically short circuit the coils 274A and 274B if there is contact between the coil and the plate. It is noted that this isolating material may not be necessary if the conducting wires or conducting elements of the coils are isolated electrically by a suitable material. When a time varying electrical current is passed in the coils 274A and 274B, eddy currents are generated in the electrically conducting plates 272A and 272B and a force is generated pushing the plates away from the coils. If the electrical current in the coils 274A and 274B periodically changes, the plates vibrate or oscillate and the elastic walls of the moving member 280 also vibrate. When the pressure oscillation generating unit 270 is disposed within a the vagina 101 such that the cavity 278 is directed towards the cervix 102 (see FIG. 3), pressure oscillations are generated in the vaginal chamber defined by the cavity 278, part of the walls of the vagina 101 and the cervix 102. The pressure oscillations act to change the flow properties of menses which results in increase menses flow rate out of the uterus 103 through the cervical canal, resulting in increase menses flow and the shortening of the duration of the menstruation period.

A printed circuit board (PCB) 275 is disposed in the housing 252. The PCB 275 is suitably electrically connected to the battery 254 to receive electrical power from the battery 254 (the electrical connections are not shown for the sake of clarity of illustration). The PCB 275 is electrically connected to the coils 274A and 274B (the electrical connections are not shown in FIGS. 19-22 for the sake of clarity of illustration) for providing suitable electrical signals to the coils and for controlling the movements or vibrations of the walls of the movable member 280 and the frequency and wave shape and (optionally) the duty cycle of the pressure oscillations generated within the vaginal chamber by the movable member 280. The PCB 275 may include a remotely actuatable switch (such as, for example the switching unit 210 of FIG. 14) that may be implemented as a magnetically actuated switch as disclosed hereinabove, however, any other type of remotely actuatable switching device may be used, as is known in the art. The PCB 275 also includes a controller or a frequency generating unit (not shown in detail), such as for example the frequency generating unit 212 of FIG. 14 which controls the parameters of the electrical signals applied to the coils 274A and 274B, such that the movable member 280 may generate any desired type of pressure oscillations, and/or acoustic waves, and/or shock waves, and/or pressure waves of a desired frequency or frequencies as disclosed in detail hereinabove and hereinafter.

A pulling cord 52 (see also FIG. 7) may be attached to the bottom end 252B of the housing 252 for assisting the removal of the pressure oscillations generating unit 270 from the vagina 101 as disclosed hereinabove.

It is noted that the wiring of the connections of the coils 274A and 274B to the PCB 275 is arranged such that the polarity and phase of the currents flowing in the coils 274A and 274B are suited to optimize the displacement of air and/or fluids included in the vaginal chamber and the resulting pressure oscillations.

Reference is now made to FIGS. 23-27. FIG. 23 is a schematic side view illustrating a pressure oscillations generating unit usable in the devices of the present application and including a box-like elastic member having two coils and also including two permanent magnets, in accordance with another embodiment of the pressure oscillations generating unit of the present application. FIG. 24 is a schematic cross sectional view of the pressure oscillations generating unit of FIG. 23 taken along the line XXIV-XXIV. FIG. 25 is another schematic side view illustrating the pressure oscillations generating unit of FIG. 23. FIG. 26 is a schematic cross sectional view illustrating the pressure oscillations generating unit of FIG. 23 taken along the line XXVI-XXVI. FIG. 27 is a schematic top view of the pressure oscillations generating unit of FIG. 26 as seen from the direction represented by the arrow M of FIG. 24.

Turning to FIG. 23, the pressure oscillations generating unit 300 includes a housing 252 which is a cylindrical housing having an opening at one end 252A. The structure of the housing 252 is as described in detail hereinabove. A power source such as a battery 254 is disposed within the housing 252. The power source may be any suitable type of compact power source as disclosed in detail hereinabove. In the exemplary embodiment illustrated in FIGS. 23-27, the battery 254 is a standard N type battery, but any other type of battery may be used.

The pressure oscillations generating unit 300 also includes a movable member 310. The movable member 310 is shaped like a rectangular box flaring at an open end 310A thereof, and closed at another end 310B thereof. However, other suitable shapes may also be used. The movable member 300 may be a thin elastic membrane made from a suitable biocompatible elastic material, such as but not limited to Milar® or any other type of elastic biocompatible plastic or polymer based material known in the art or the like. The flaring end 310A of the movable member 300 is sealingly attached to the opening at the end 252A of the housing 252 (such as, for example by suitable gluing or welding or any other method of sealably attaching method known in the art). An open cavity 320 is formed within the movable member 310.

Two flat thin electrical coils 304A and 304B are attached to or glued on opposite sides of the movable member 310. The coils 304A and 305B are rectangular in shape but may also be shaped as elliptical coils round coils or as coils having other suitable shapes. Two permanent magnets 306A and 306B are rigidly attached to the housing 252 such that the magnet 306A is disposed adjacent to and facing the coil 304A and the magnet 306B is disposed adjacent to and facing the plate 272B. The coils 304A and 304B are preferably planar coils, but other types of non-planar coils may also be used. The coils 304A and 304B are preferably wound from thin insulated electrically conducting wires (not shown in detail), but may also be planar or non-planar coils printed on a thin printed circuit board (PCB) as is known in the art, or any other type of suitable coils. It is noted that the windings of the electrical wires or conductors included in the coils 304A and 304B are not shown in detail in FIGS. 19-22 for the sake of clarity of illustration.

When a time varying electrical current is passed in the coils 304A and 304B, a magnetic field is generated in the coils having a polarity depending on the current direction and the coil geometry and windings direction and a force is generated pushing the coils 304A and 304B towards or away from the permanent magnets 306A and 306B, respectively (the direction of the force may depend, inter alia, on the polarity of the magnetic field of the permanent magnets 306A and 306B, and on the direction of current flow in the coils 304A and 304B. If the electrical current in the coils 304A and 304B periodically changes, the side walls of the movable member 310 to which the coils 304A and 304B are attached vibrate or oscillate. When the pressure oscillation generating unit 300 is disposed within the vagina 101 such that the opening of the cavity 320 is directed towards the cervix 102 (see FIG. 3), pressure oscillations are generated in the vaginal chamber defined by the cavity 320, part of the walls of the vagina 101 and the cervix 102. The pressure oscillations act to change the flow properties of menses which results in increase menses flow rate out of the uterus 103 through the cervical canal, resulting in increase menses flow and the shortening of the duration of the menstruation period.

A printed circuit board (PCB) 305 is disposed in the housing 252. The PCB 305 is suitably electrically connected to the battery 254 to receive electrical power from the battery 254 (the electrical connections are not shown for the sake of clarity of illustration). The PCB 305 is suitably electrically connected to the coils 304A and 304B (the electrical connections are not shown in FIGS. 23-27 for the sake of clarity of illustration) for providing suitable electrical signals to the coils 304A and 304B and for controlling the movements or vibrations of the walls of the movable member 310 and the frequency and wave shape and (optionally) the duty cycle of the pressure oscillations generated within the vaginal chamber by the movable member 310. The PCB 305 may include a remotely actuatable switch (such as, for example the switching unit 210 of FIG. 14) that may be implemented as a magnetically actuated switch as disclosed hereinabove, however, any other type of remotely actuatable switching device may be used, as is known in the art. The PCB 305 also includes a controller or a frequency generating unit (not shown in detail), such as for example the frequency generating unit 212 of FIG. 14 which controls the parameters of the electrical signals (electrical currents) applied to the coils 304A and 304B, such that the movable member 310 may generate any desired type of pressure oscillations, and/or acoustic waves, and/or shock waves, and/or pressure waves of a desired frequency or frequencies as disclosed in detail hereinabove and hereinafter.

A pulling cord 52 (see also FIG. 7) may be attached to the bottom end 252B of the housing 252 for assisting the removal of the pressure oscillations generating unit 300 from the vagina 101 as disclosed hereinabove.

It is noted that the wiring of the connections of the coils 274A and 274B to the PCB 305 is arranged such that the polarity and phase of the currents flowing in the coils 304A and 304B are suited to optimize the displacement of air and/or fluids included in the vaginal chamber and the resulting pressure oscillations.

It is also noted that in accordance with another embodiment of the pressure oscillations generating unit of the present application, the permanent magnets 306A and 306B may be replaced with two coils (not shown) attached to the walls of the movable member 310. These coils which may be fed with suitable electrical currents by connecting them to current generating circuitry disposed on the PCB 305 such that they function as an electromagnet to generate a magnetic field (optionally) similar to the magnetic field of the permanent magnets 306A and 306B. However, when such a configuration having four coils is implemented, the current passed in the coils replacing the permanent magnet need not necessarily be a DC current, rather oscillating currents or other types of time varying (or pulsatile) currents may be passed through all four currents to optimize current consumption and to optimize the pressure oscillations amplitude.

It is noted that while the tampon-like devices disclosed hereinabove (such as for example the device 500 of FIG. 1) which include an absorbent element sleeve or pad, (such as, for example, the compressed cotton sleeve 51 of FIG. 1) are convenient for use, they are not intended to limit the devices of the present application. For example, any of the pressure oscillations generating units disclosed in the preset application may be used to achieve the intended desired menses period duration shortening effect without including any absorbent member or sleeve or pad as part of the device placed in the vagina 101.

In accordance with another embodiment of the menses duration shortening devices of the present application, the dimensions of any of the pressure oscillations generating units disclosed herein may be modified such they are within the range of dimensions which may be conveniently and comfortably inserted into the vagina 101. For example, any of the pressure oscillations generating units illustrated in FIGS. 16-27 may be adapted for convenient insertion inserted into the vagina 101. In such a case, the menstruation period duration shortening device may be a pressure oscillations generating unit, such as but not limited to any of the pressure oscillations generating units 250, 270 and 300 (of FIGS. 17, 20, and 24, respectively) which is adapted in it's dimensions for convenient insertion into a vagina. It is noted that the dimensions of such pressure oscillations generating units may be similar to the dimensions of typical regular tampons known in the art, but they may be made from a non-absorbent material and configured to be hermetically sealed to prevent entry of any vaginal fluids or menstrual secretions into the pressure oscillations generating unit to prevent any electrical circuitry shorting effects and/or the delivering of electrical currents to the vagina (an exemplary embodiment of such a tampon-less device is disclosed in detail in FIG. 37, hereinbelow).

Figure 28A:
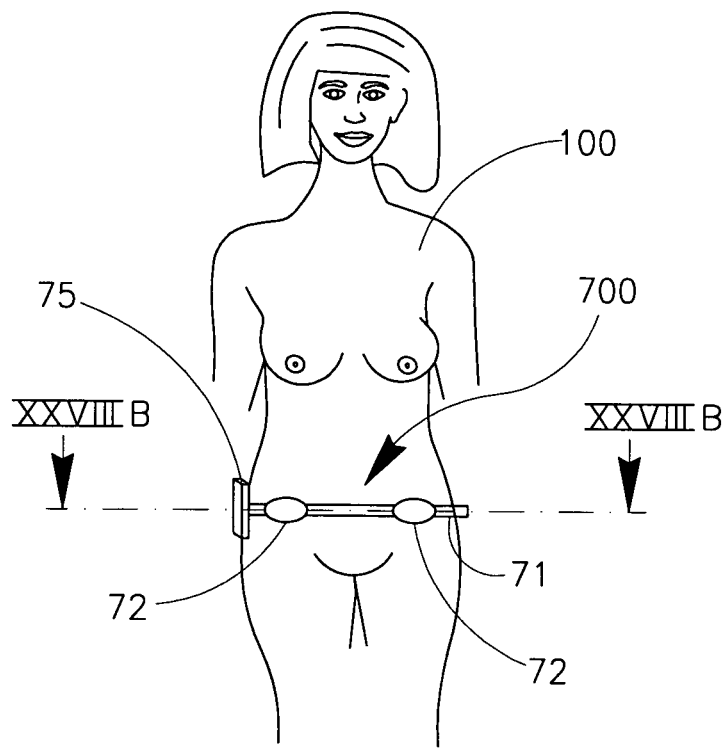
FIG. 28A is a schematic illustration of a woman wearing an active belt around her pelvis, according to another embodiment of the devices of the present application.
Figure 28B:
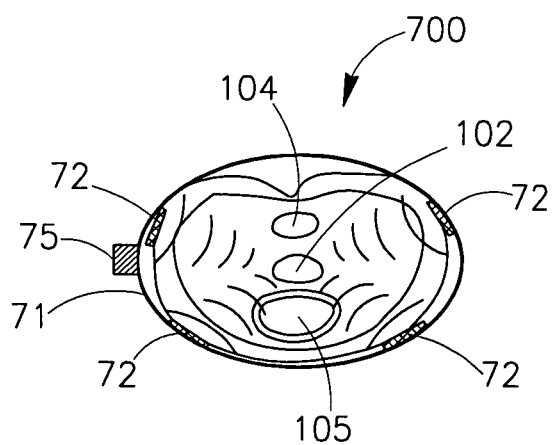
FIG. 28B is a schematic cross sectional side view of the woman and the active belt of FIG. 14 taken along the line XXVIIIB-XXVIIIB.

Reference is now made to FIGS. 28A-28B. FIG. 28A is a schematic illustration of a woman wearing an active belt around her pelvis, according to another embodiment of the devices of the present application, and FIG. 28B is a schematic cross sectional side view of the woman and the active belt of FIG. 28A taken along the line XXVIIIB-XXVIIIB.

FIGS. 28A-28B illustrate several anatomical details, such as the cervix 102, rectum 104, and bladder 105. The woman 100 wears an active belt 700 around her pelvis, according to another embodiment of the active menstruation duration shortening devices of the present application. The active belt 700 includes several vibration generating units 72 that are attached to an elastic belt 71. The vibration generating units 72 are designed to generate the following vibrational waves:
  a. Pressure waves.
  b. Shear waves.

The frequency and amplitude of each of the wave types is preferably between 0.1 Hz to 10 kHz and 0.1 to 2 mm, respectively, but other different vibration frequencies and amplitudes may also be used in the active belt of the present application. The vibration generating units 72 are all directed towards the cervix 102 thus enabling the transfer of sufficient energy through the tissue giving rise to the vibration of the cervix.

The external vibration of the cervix achieves the desired change of the effective viscosity of the menses fluid as explained hereinabove by changing the flow properties of the non-Newtonian menses secretions. This accelerates the flow of menses through the cervical lumen and thus effectively shortens the duration of menstruation.

The vibration generating units 72 may be any type of vibrating elements configured for delivering mechanical vibrations to the tissues of the woman 100 (including, but not limited to, piezoelectric transducers, mechanical and/or electromechanical vibrating elements and/or transducers, and the like) are disposed in contact with the skin of the woman 100 and are all directed towards the cervix 102, enabling the transfer of sufficient vibrational mechanical energy through the tissue to cause or induce vibrations of the cervix 102. The vibration emitters 72 may be operated by a regular switch, which may be connected to a power supply (not shown) through a transformer (not shown) or to a battery pack (not shown). For example, a control unit 75 attached to the elastic belt 71 may include a power source (not shown) such as any of the electrical power sources disclosed in detail hereinabove, an activating switch (not shown) for controlling power application from the power source included in the control unit 75 to the vibration emitters It is emphasized that active belt 700, with the necessary changes and modifications, may also be put on other places of the human body for reducing the effective viscosity of liquids or fluids in other body parts.

Besides the theoretical analysis of the physical behavior and operational parameters of the devices required and vaginal chamber physical behavior, the inventor has also performed in-vitro and in-vivo experiments which are disclosed in detail hereinafter.

Experiment 1

The in-vitro experiment was aimed at carry out an initial optimization study of the shape, amplitude and frequency of the pressure oscillations usable in the devices of the present application. In addition, the characteristics of the tissue debris within the menses were analyzed, as was the effect of the pressure oscillations on the debris characteristics.

Figure 29:
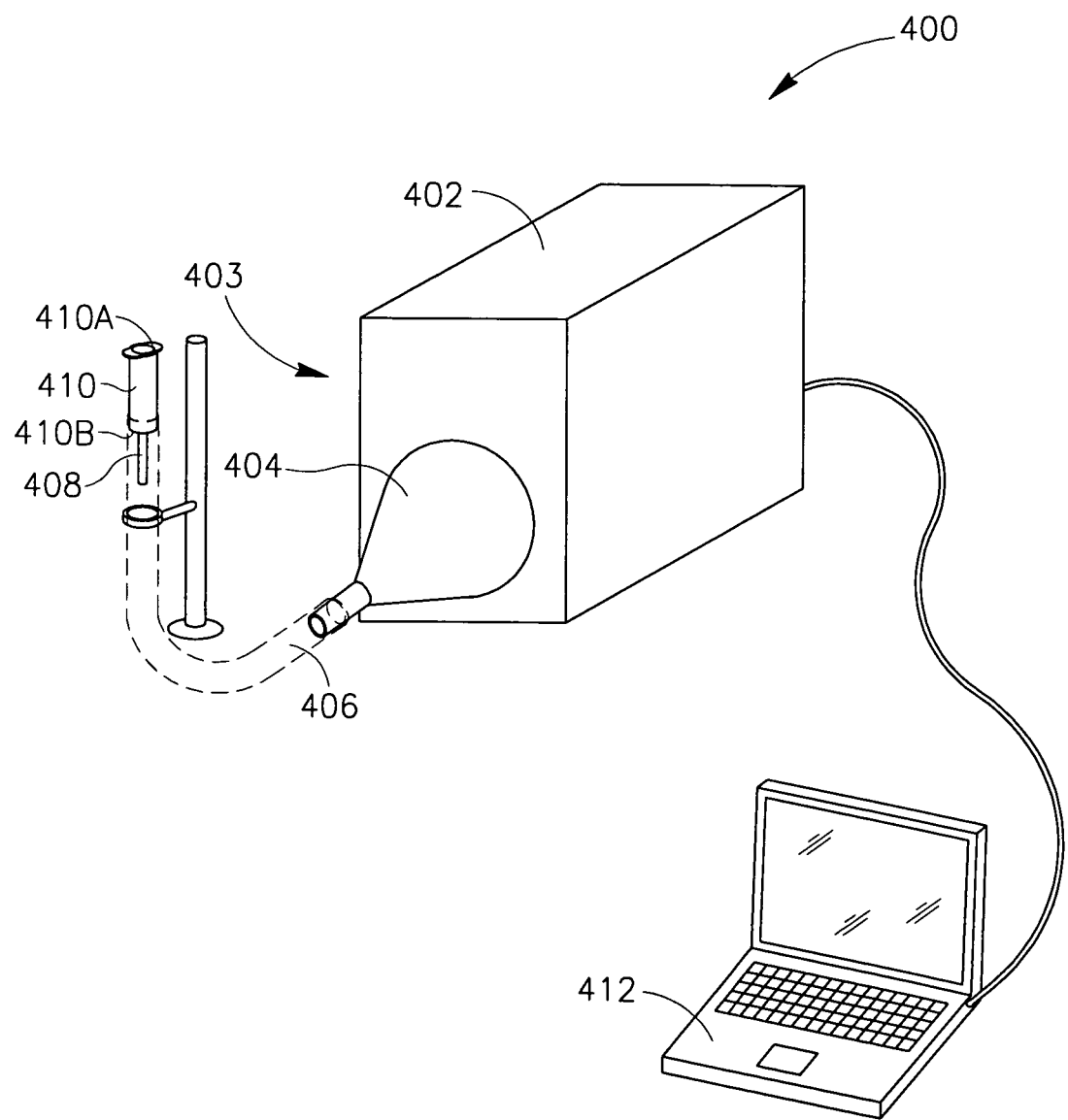
FIG. 29 is a schematic isometric diagram illustrating the components of an experimental setup used for performing EXPERIMENT 1.

Reference is now made to FIG. 29 which is a schematic diagram illustrating the components of an experimental setup used for performing EXPERIMENT 1.

The experimental setup 400 includes a transducer 403, a vaginal applicator 406, a cervical model 408, a uterus model 410 and a controller 412. The pressure oscillation transducer 403 includes a sub-woofer 402 and a funnel coupler 404 sealingly attached to the subwoofer 402. The sub-woofer 402 was a "PSB alpha subsonic 5 sub-woofer". The subwoofer 402 comprises a 378×314×419 mm sized wooden box. All outlets of the box were sealed through the use of rigid materials and glued into place using a commercial silicone sealing compound. The circular speaker, located on the side of the box of the subwoofer 402 is 25 cm in diameter, and includes a polypropylene cone, a rubber surrounded 38 mm diameter voice coil and both a 794gr magnet and a shielding magnet.

The total internal volume of the sub-woofer 402 is 28.6 liter and it is rate at 150 Watt nominal power.

The speaker port of the sub-woofer 402 was covered with a 27 cm diameter funnel coupler 404 and sealed using a silicon sealing compound. The narrow outlet of the funnel coupler 404 was connected to a PVC tube (commercially available from Reshafim, Israel) having 16 and 19 mm inner and outer diameters, respectively.

A vaginal applicator 406 is sealingly attached to the funnel 404 on one end and is sealingly attached to the uterus model 410. The cervical model 408 is fluidically coupled to the uterus model 410 as shown. The uterus model 410 was implemented as a syringe (10 ml volume from PLASTIPAK. The syringe plunger was removed and discarded and the resulting rigid tube of the syringe opens to the atmosphere at one end, and was connected at the other end 410B to a needle connecting port (not shown) with an inner diameter of 3.5 mm. The outer diameter of the syringe was 16 mm and the length of the syringe was 10 cm.

The cervix model 408 was a tube with an inner diameter 3 mm. The Young modulus is typically 1 Mpa. In the associated literature the cervix muscle tissue is described as similar to cartilage. The cervix model 408 was connected to the needle port (not shown in detail) of the syringe used as the uterus model 410. The tube implementing the cervix model 408 is suspended in the inner cavity of the vaginal applicator 406. The cervical model 408 was a rigid tube with small bending capabilities. The tube was 4 cm long and had a 3 mm inner diameter. The vaginal applicator 406 was implemented by a rigid tube made from polyvinyl chloride (PVC) which had 16 mm and 19 mm inner and outer diameters, respectively and a length of 20 cm. The tube was sealingly coupled connected to the syringe simulating the uterus model 410 as illustrated in FIG. 29.

The pressure oscillations were generated by the sub-woofer 402 and were controlled by the controller 412 which was implemented on a laptop computer (Macintosh 2.16 GHz Intel Core 2 Duo running Mathematica® software used to generate the required wave shapes and frequencies) The headphone port of the laptop computer was connected to the low level input jacks of the subwoofer 402. The frequency and amplitude of the electrical signals delivered to the subwoofer 402 were controlled through the use of the laptop computer implementing the controller 412. Real menses fluid and debris were freshly collected from a menstruating female subject and were used in the model by placing the menses within the syringe used as the uterus model 410.

Anatomical and Physiological Simulation:

The anatomical simulation model is divided into three components: the uterus, the cervix, and the menses. The uterine cavity is a potential cavity, i.e., the uterine inner walls normally touch each other. The endometrial layer slowly grows in the inner part of the uterus. During menstruation, two types of forces affect the menses flow: the uterine thick muscle layer contractions and gravitational forces. According to literature, the inner pressure inside the uterus during menstruation is in the range of 50-200 mmHg.

In order to simulate accurately the uterine cavity, the above physiological and anatomical properties of the uterus must be taken in to account. Nevertheless, since the natural contractions of the uterus facilitate the flow of menses through the cervix, the pressure oscillations effect, if shown without the contractions will evidently work with the contractions as well. Hence, the naturally applied contractions by the uterus and the inner uterine changes in pressure can be neglected and only the gravitational forces are considered.

The experimental procedure was used for characterizing the tissue particles before and after applying pressure oscillations, and for examining the effects of application of different pressure oscillations on the tissue fragments included in the menses.

Characterizing the Tissue Fragments:

The menses fluid was pre-collected from a female volunteer. The fluid was divided to liquids and tissue fragments by the use of a sieve having a pore size of approximately 1 mm by 1 mm. The pieces of tissue were measured. The average size of tissue pieces was found to be 1 cm. Therefore, the pieces of tissue were manually ordered and cut if needed to approximately 1 cm in length when the rest was discharged. The goal of this procedure was to create a somewhat standard base line.

In total 6 tissue fragments were used. Each was taken separately and placed gently on the bottom of the syringe (uterus model 410) near the inlet of the cervical model 408. Real menses fluids with no tissue particles was then purred into the syringe slowly, so the elevation of static pressure would be very slow and controlled. The menses added moved the tissue into its location at the inlet of the cervical model 408. As a result, the tissue pieces blocked the 3 mm diameter opening of the cervical model 408 and the menses fluid was accumulated in the syringe.

Two tests were then preformed on the system: 3 cm height of menses fluid was purred in the syringe and left to stand for fifteen minutes. This showed that without any external force the tissue fragments completely block the cervix model 408 preventing any fluids from flowing.

The second test was to examine, what static pressure is needed in order to force the tissue through the cervical model 408. For this part, fluid was added into the syringe to increase the static pressure applied to the tissue pieces. The expression "drain pressure" is used hereinafter to refer to the static pressure which was measured when the tissue fragment was forced out from the cervical model 408. Each experiment was carried out five times on each tissue fragment. In addition the same tests were preformed on each one of the used tissue fragments after they were exposed to pressure oscillations, and their drain pressure was measured again after exposure of these tissue fragments to pressure oscillations.

Examining the Effect of Different Pressure Oscillations

The tissue fragments that were used in the experiments were taken in the same manner as described hereinabove and placed inside the syringe of the uterus model 410. Menses was then poured into the syringe to a height of 1 cm lower then the average "draining pressure" height found previously. This was done to make sure that the tissue fragment is placed in the cervical model 408 in such a way that sufficient amount of pressure is needed to open it. Then, the menses fluid level in the syringe of the uterus model 410 was reduced to a height gravitationally equivalent to 3 cm of water. This was done with the use of a pipette without touching the tissue fragment or changing its position. The reduction in static pressure was performed in order to make sure that the pressure oscillations applied to the cervical outlet are the cause of "opening" the cervix and not the static pressure applied by the liquids.

After the particle and the menses fluid were ready inside the syringe of the uterus model 410, different pressure oscillations were applied using the sub-woofer 402. The pressure oscillations were applied through the PVC tube of the vaginal applicator 406 to the outlet of the cervical model 408. The tested range of pressure oscillations was 10 Hz to 300 Hz with 10 Hz jumps.

Six different pressure oscillation waveforms were applied: a sine wave, a sawtooth wave with a slow rising phase and a fast falling phase, a sawtooth wave with a fast rising phase and a slow falling phase, a sine wave which was amplitude modulated by a 1 Hz sawtooth with slow rise and fast fall, and a sine wave which was amplitude modulated by a 1 Hz sawtooth wave with a fast rising phase and a slow falling phase, and a square wave with a 50% duty cycle.

The signal peak amplitude which was fed to the input terminals of the sub-woofer 402 was constant and was set to the maximum amplitude possible for the sub-woofer 402. For each individual particle and each individual waveform used, a range was found where the particle was affected by the pressure oscillations and the tissue has undergone a "drainage pressure" event.

Results of Characterizing the Tissue Particles:

The total amount of tissue particles used in this experiment was six particles.

Each particle was tested five times to examine its resistance to static pressure.

The results are summarized in TABLE 1 below:

TABLE 1

| particle No. | Drainage pressure (cmH$_2$O) | Particle length | Particle width | Mean pressure (cm H$_2$O) |
|---|---|---|---|---|
| 1 | 4 | 1 cm | 3 mm | 5.3 |
| 1 | 6 | | | |
| 1 | 4 | | | |
| 1 | 9 | | | |
| 1 | 3.5 | | | |
| 2 | 7 | 1 cm | 5 mm | 6.4 |
| 2 | 5 | | | |
| 2 | 6 | | | |
| 2 | 7 | | | |
| 2 | 7 | | | |
| 3 | 7 | 5 mm | 5 mm | 6.4 |
| 3 | 4 | | | |
| 3 | 7 | | | |
| 3 | 7 | | | |
| 3 | 7 | | | |
| 4 | 18 | 1 cm | 5 mm | 14.9 |
| 4 | 14 | | | |
| 4 | 14 | | | |
| 4 | 14 | | | |
| 4 | 14.5 | | | |
| 5 | 5.5 | 8 mm | 4 mm | 6.4 |
| 5 | 6 | | | |
| 5 | 7.5 | | | |
| 5 | 5 | | | |
| 5 | 8 | | | |
| 6 | 4 | 6 mm | 4 mm | 4.8 |
| 6 | 5 | | | |
| 6 | 2.5 | | | |
| 6 | 8 | | | |
| 6 | 4.5 | | | |

The results of determining the particle characteristics after exposure to the series of pressure waves are summarized in TABLE 2. The parameters of the pressure wave types used on specific particles are summarized in TABLE 3 below

TABLE 2

| Particle No. | Drainage Pressure (cmH$_2$O) | Mean Pressure (cmH$_2$O) |
|---|---|---|
| 1 | 1 | 4.5 |
| 1 | 8 | |
| 1 | 4 | |
| 1 | 0.5 | |
| 1 | 9 | |
| 2 | 0 | 3.8 |
| 2 | 2 | |
| 2 | 6 | |
| 2 | 7 | |
| 2 | 4 | |
| 3 | 10 | 4.2 |
| 3 | 2 | |
| 3 | 1 | |
| 3 | 8 | |
| 3 | 0 | |
| 4 | 5 | 7.1 |
| 4 | 10 | |
| 4 | 11 | |
| 4 | 3 | |
| 4 | 6.5 | |
| 5 | 0 | 3.0 |
| 5 | 1 | |
| 5 | 7 | |
| 5 | 2 | |
| 5 | 5 | |
| 6 | 1 | 2.5 |
| 6 | 4 | |
| 6 | 2.5 | |
| 6 | 2 | |
| 6 | 3 | |

TABLE 3

| Particle no. | Wave shape | Frequency range draining the tissue | Max Duration |
|---|---|---|---|
| 1 | Sine | 10-230 Hz | 3 sec |
| 2 | Sawtooth (slow rise fast fall) | 10-260 Hz | 5 sec |
| 3 | Sawtooth (fast rise slow fall) | 10-250 Hz | 2 sec |
| 4 | Sine + Sawtooth (slow rise fast fall constant 1 Hz) | 20-230 Hz | 10 sec |
| 5 | Sine + Sawtooth (fast rise slow fall constant 1 Hz) | 10-220 Hz | 3 sec |
| 6 | Square | 50-150 Hz | 20 sec |

As may be seen from TABLES 1-3 above, the resistance to pressure was reduced, moreover, the particles were observed to have different color and their three dimensional shape has changed following pressure application but these observed effects could not be quantified without the proper measurement tools.

While EXPERIMENT 1 described above is an exploratory preliminary experiment, the following conclusions may be drawn:

The static pressure resistance of tissue fragments depends on to the fragments' position inside or at the cervical model inlet. Particles that are more round are more likely to have consistent pressure resistance characteristics. After the tissue particles were exposed to pressure oscillations above 100 Hz, their measured resistance to static pressure was reduced at certain positions.

Pressure oscillations are shown to create "drainage pressure" conditions on the tissue fragments. As shown, pressure oscillations cause tissue fragments to flow through the cervix model. This may possibly be the result of the following effects on menses flow: (a) The effective viscosity of the suspension fluid is reduced due to the "streaming" effect applied by the fluid vibrations induced by the oscillatory pressure gradient across the cervix model. (b) The vibration of the fluid allows for resettling of the tissue debris in the cervical inlet, which may also facilitates the menses flow through the cervix model used.

In order to extend the present study of the effects of pressure oscillations on menses flow, an additional in-vivo experiment was performed as disclosed hereinafter.

Experiment 2

In this experiment, the menses flow of a female volunteer was compared, with and without the application of pressure oscillations to the vagina.

In the first part of EXPERIMENT 2, a normal menstruation period of a 36 years old parous female volunteer, who experiences regular menstruations but does not normally experiences dysmenorrhea was followed by measuring the amount of menses fluid at time intervals of about six hours by using a commercial menstrual cup inserted into the vagina. The parameters determined during the normal menstrual period (the control period) included, for each measurement, the total volume of menses collected in the single measurement (in ml) and the menses flow rate in ml/hour (computed from the collected menses volume divided by the collection period duration for each single measurement).

The results of the first part of the experiment (normal menses control) are summarized in TABLE 4 below.

TABLE 4

| Sample number | Date | Hr. | Time (hours) | Amount Of collected menses (ml) | Menses Flow Rate (ml/hr.) | Remarks |
|---|---|---|---|---|---|---|
| 1 | Mar. 11, 2007 | 22:00 | | 1 | | First day |
| 2 | Apr. 11, 2007 | 8:00 | 10 | 0.5 | 0.05 | Night |
| 3 | Apr. 11, 2007 | 12:00 | 4 | 1 | 0.25 | |
| 4 | Apr. 11, 2007 | 18:00 | 6 | 0.5 | 0.083 | |
| 5 | May 11, 2007 | 6:00 | 12 | 2 | 0.167 | Night |
| 6 | May 11, 2007 | 12:00 | 6 | 1.5 | 0.25 | |
| 7 | May 11, 2007 | 20:00 | 8 | 8 | 1 | |
| 8 | Jun. 11, 2007 | 7:00 | 11 | 11 | 1 | Night |
| 9 | Jun. 11, 2007 | 13:00 | 6 | 7.5 | 1.25 | |
| 10 | Jun. 11, 2007 | 18:00 | 5 | 5 | 1 | |
| 11 | Jul. 11, 2007 | 6:00 | 12 | 2.5 | 0.21 | Night |
| 12 | Jul. 11, 2007 | 12:00 | 6 | 1 | 0.167 | |
| 13 | Jul. 11, 2007 | 18:00 | 6 | 0.5 | 0.083 | |

In the second part of the in-vivo experiment, pressure oscillations were introduced into the vagina of the same volunteer at different times during menstruation, such that an oscillatory pressure gradient was induced on the cervix. The second part of the experiment was performed two menses cycles apart from the first part of the experiment. The first part of the experiment was conducted starting on Nov. 3, 2007 and the second part of the experiment using pressure oscillations was conducted starting on Dec. 28, 2007.

Figure 30:
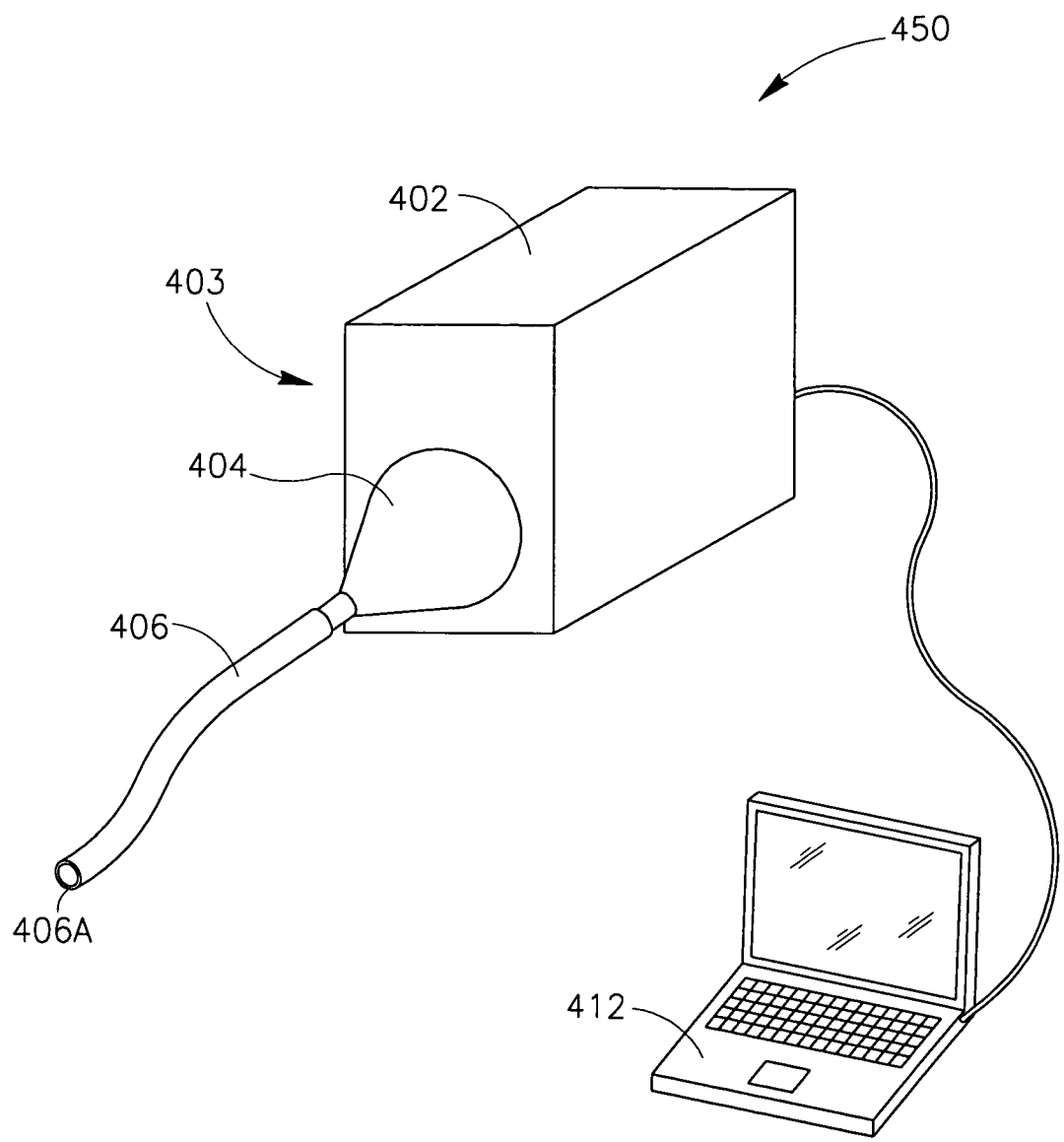
FIG. 30 is a schematic isometric view of an experimental setup used for applying acoustic pressure waves in-vivo to a vagina of a menstruating female subject.

Reference is now made to FIG. 30 which is a schematic isometric view of an experimental system used for applying pressure oscillation in-vivo to a vagina of a menstruating female subject.

The experimental system 450 includes the same transducer 403, controller 412, funnel coupler 404 and vaginal applicator 406 as described in detail hereinabove for EXPERIMENT 1. The parts representing the uterus model 410 and cervical model 408 of EXPERIMENT 1 were disconnected from the end 406A of the vaginal applicator 406. The open end 406A of the vaginal applicator 406 was inserted into the vaginal cavity of a 36 years old parous female volunteer, who experiences regular menstruations but does not normally experiences dysmenorrhea, and pressure oscillations were applied to the vaginal chamber formed between the end 406A of the vaginal applicator 406 the vaginal walls and the cervix of the volunteer.

Different sinusoidal pressure oscillations were applied at different times. The pressure oscillations were applied for time periods of 10 minutes or 15 minutes. The menses drained into the vagina and were collected through the use of a commercial menstrual cup. The amount of menses was then measured using a 1.0 ml measuring syringe.

TABLE 5 below summarizes the amount of menses measured at different times and the application of various oscillatory pressure waves as described above. The onset of menstruation was marked as time zero.

TABLE 5

| DAY | Hr (hours) | Minute | Flow from previous entry (ml) | Pressure oscillations |
|---|---|---|---|---|
| Dec. 28, 2007 | 0 | 0 | 1 | 0 |
| Dec. 29, 2007 | 6 | 10 | 0.1 | 40 Hz |
| Dec. 29, 2007 | 6 | 20 | 0.1 | 80 Hz |
| Dec. 29, 2007 | 6 | 40 | 0.1 | 100 Hz |
| Dec. 29, 2007 | 7 | 0 | 0 | 0 |
| Dec. 29, 2007 | 11 | 10 | 5 | 0 |
| Dec. 29, 2007 | 11 | 20 | 0 | 80 Hz |
| Dec. 29, 2007 | 12 | 30 | 0.5 | 0 |
| Dec. 29, 2007 | 12 | 45 | 0.2 | 0 |
| Dec. 29, 2007 | 15 | 43 | 1.80 | 0 |
| Dec. 29, 2007 | 15 | 53 | 0.1 | 80 Hz |
| Dec. 29, 2007 | 16 | 5 | 0.05 | 100 Hz |
| Dec. 29, 2007 | 16 | 18 | 0.05 | 40 Hz |
| Dec. 29, 2007 | 16 | 24 | 0 | 1 Hz |
| Dec. 29, 2007 | 16 | 32 | 0.01 | 60 Hz |
| Dec. 29, 2007 | 16 | 41 | 0.4 | 80 Hz |
| Dec. 29, 2007 | 17 | 0 | 0.01 | 0 |
| Dec. 29, 2007 | 17 | 15 | 0.02 | 0 |
| Dec. 29, 2007 | 17 | 35 | 0.25 | 0 |
| Dec. 29, 2007 | 18 | 0 | 0.4 | 0 |
| Dec. 29, 2007 | 18 | 15 | 0.3 | 0 |
| Dec. 29, 2007 | 18 | 30 | 0.25 | 0 |
| Dec. 29, 2007 | 18 | 48 | 0.3 | 80 Hz |
| Dec. 29, 2007 | 18 | 5 | 0.4 | 0 |
| Dec. 29, 2007 | 18 | 23 | 0.6 | 0 |
| Dec. 29, 2007 | 18 | 46 | 0.5 | 0 |
| Dec. 29, 2007 | 19 | 0 | 0.25 | 80 Hz |
| Dec. 29, 2007 | 19 | 7 | 0.25 | 80 Hz |
| Dec. 29, 2007 | 19 | 22 | 0.25 | 0 |
| Dec. 29, 2007 | 19 | 41 | 0.35 | 0 |
| Dec. 29, 2007 | 20 | 0 | 0.25 | 0 |
| Dec. 29, 2007 | 20 | 16 | 0.25 | 0 |
| Dec. 29, 2007 | 20 | 50 | 0.25 | 0 |
| Dec. 29, 2007 | 22 | 30 | 0.75 | 0 |
| Dec. 29, 2007 | 22 | 45 | 0.25 | 0 |
| Dec. 29, 2007 | 23 | 15 | 0.25 | 0 |
| Dec. 29, 2007 | 25 | 30 | 0.5 | 0 |
| Dec. 30, 2007 | 32 | 45 | 1.75 | 0 |
| Dec. 30, 2007 | 34 | 35 | 0.25 | 0 |
| Dec. 30, 2007 | 36 | 17 | 0.4 | 0 |
| Dec. 30, 2007 | 36 | 25 | 0.2 | 80 Hz |
| Dec. 30, 2007 | 36 | 40 | 0.5 | 80 Hz |
| Dec. 30, 2007 | 37 | 5 | 0.2 | 0 |
| Dec. 30, 2007 | 38 | 45 | 0.7 | 0 |
| Dec. 30, 2007 | 38 | 52 | 0.25 | 80 Hz |
| Dec. 30, 2007 | 39 | 4 | 0.35 | 80 Hz |
| Dec. 30, 2007 | 40 | 5 | 0.05 | 0 |
| Dec. 30, 2007 | 42 | 30 | 0.15 | 0 |
| Dec. 30, 2007 | 51 | 0 | 0.7 | 0 |
| Dec. 31, 2007 | 57 | 30 | 0.5 | 0 |
| Dec. 31, 2007 | 61 | 30 | 0.5 | 0 |
| Dec. 31, 2007 | 67 | 30 | 0.5 | 0 |

A comparison between the results summarized in TABLE 4 and TABLE 5 reveals a clear physiological effect to the application of the pressure oscillations of the present invention.

Figure 31:
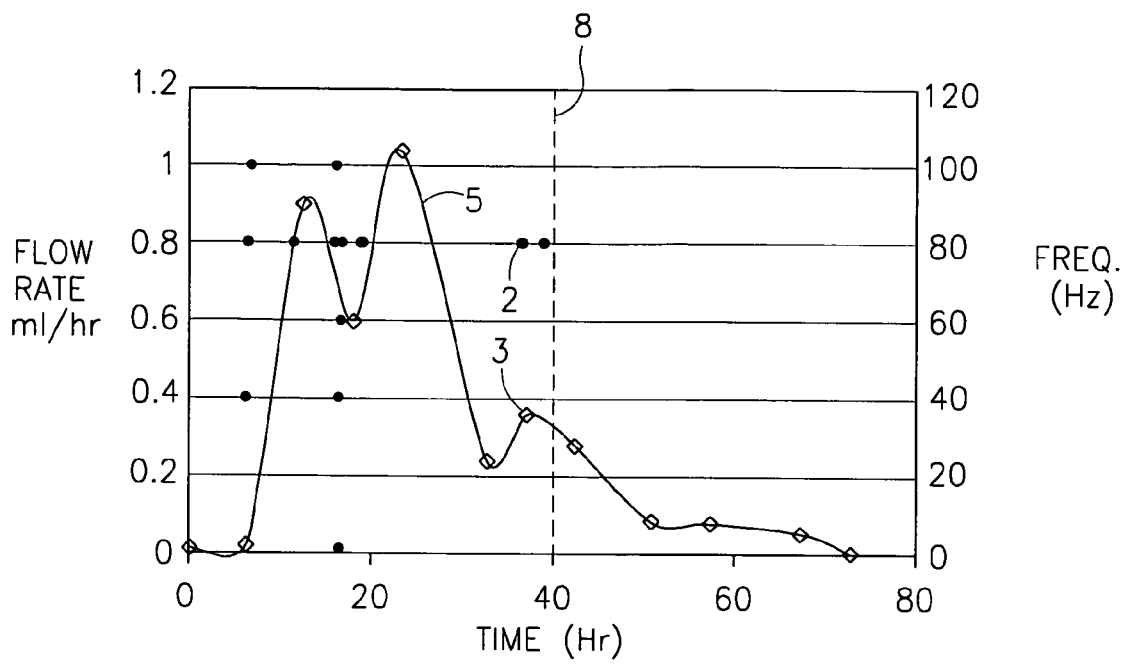
FIG. 31 is a schematic graph illustrating the results of an in-vivo experiment measuring the flow of menses in the presence of acoustic pressure waves applied to the vagina of a menstruating female.
Figure 32:
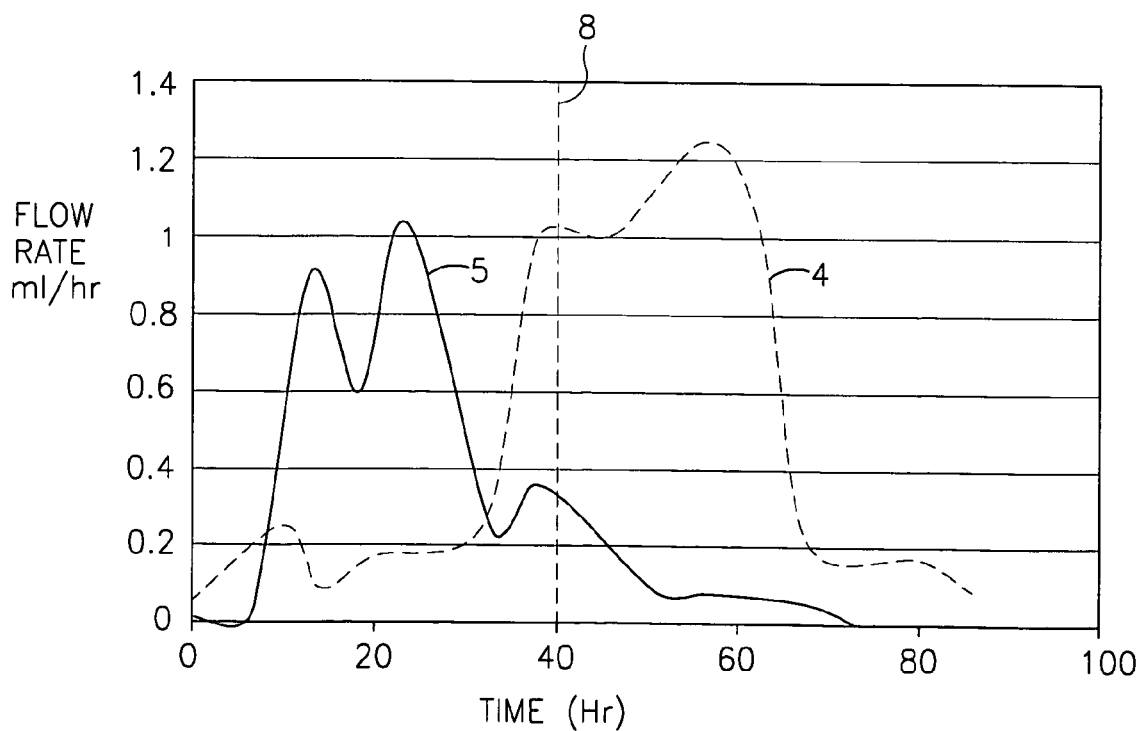
FIG. 32 is a schematic graph illustrating the results of an in-vivo experiment comparing the menses flow of a menstruating female with and without application of pressure oscillations to the vagina.

Reference is now made to FIGS. 31 and 32. FIG. 31 is a schematic graph illustrating the results of the in-vivo experiment measuring the flow of menses in the presence of acoustic pressure oscillations applied to the vagina of a menstruating female. FIG. 32 is a schematic graph illustrating the results of an in-vivo experiment comparing the menses flow of the same menstruating female with and without application of acoustic pressure waves to the vagina.

In FIG. 31, the horizontal axis represents time in hours, the left vertical axis represents the menses rate of flow in ml/hour and the right vertical axis represents the applied pressure oscillation frequency in Hz. The open rhombus symbols 3 represent individual menses flow rate data points, and the curve 5 represents a spline curve fit computed for the data points 3 (represented by the open rhombus symbols) representing the menses flow rate of TABLE 5 and the multiple filled circles 2 in the graph each represent the time of application of vaginal pressure oscillations and the frequency of the applied pressure oscillations in Hz.

In FIGS. 31-32, the dashed vertical line 8 represent the time of application of the last pressure oscillations (at forty hours from the beginning of menstruation) in the second part of the experiment, after which no more pressure oscillations were applied for the remaining time of the menstruation (but menses flow rate measurements were continued.

In FIG. 32, the horizontal axis represents time in hours and the vertical axis represents the menses rate of flow in ml/hour. The curve 4 represents a spline curve fit computed for the data points representing the menses flow rate of TABLE 4.

Normal menses flow is known to follow a typical "crescendo-decrescendo" behavior. see, for example, the article found in:

http://www.ultimatehealthguide.com/guide/womens_health/menstruation/articles_menstrual_cycle/), that is, the normal menses flow typically starts with a moderate flow rate, it then progressively increases, and then slowly tapers off. This exact behavior can be seen in the normal menstrual flow represented by curve 4 of FIG. 32. On the other hand, the menstrual flow measured in the second part of the experiment (in which pressure oscillations were applied to the vagina) represented by the curve 5 of FIGS. 31-32 has a shape and time course notably different than those of curve 4. Apparently, the peak (maximal) flow rates in the presence of pressure oscillations application are reached much earlier in the menstruation as compared to the normal menstruation, such that the bulk of the outflow under pressure oscillation application ends relatively early.

As may be clearly seen from comparing the curves 4 and 5, the total amount of hrs with any menses flow is roughly similar (about seventy two hours for curve 5 and ninety hours for curve 4). However, it is noted that no pressure oscillations were applied after forty hours in the second part of the experiment. Irrespectively, it is clear that the pressure oscillations are effective at quickly evacuating the uterus already in the early phase of the menstrual flow.

The clear evidence of the early evacuation of the uterine under pressure oscillation application does not prove that dysmenorrheic pain will be reduced, it does however strongly suggest so, since it implies that the uterus is kept free of menses and the prostaglandins they contain which are believed to cause the cramps and uterine contraction which are experienced by dysmenorrheic women.

Although the small pressure oscillation generating devices disclosed hereinabove and the large subwoofer 402 used in the experiments appear to be remarkably different, based on calculations performed by the inventor, the energy available to the small pressure oscillation generating devices from a standard N-sized battery is sufficient to produce pressure oscillations in the inner vaginal cavity that are similar to those produced by the large subwoofer used in the experimental system of FIG. 30, and for the necessary duration.

If we assume that the efficiency of producing pressure oscillations by the small pressure oscillation generating devices and by the subwoofer 402 is similar, then the following scaling may be used. The volume enclosed externally to the speaker membrane is about 2.3 liter. On the other hand, we expect the volume of the vaginal cavity formed next to the small pressure oscillation generating devices disclosed hereinabove to be about 20 ml. Thus, to get a similar pressure oscillation next to the cervix, the small pressure oscillation generating devices disclosed need about 0.01 (one hundredth) of the energy used by the sub-woofer 402, or about 1.5 Watt. This implies that in order to get an effect similar to that of the subwoofer 402, assuming the same efficiency, the smaller pressure oscillation generating devices disclosed in the present application with a power rating of a typical 1500 mWhr N-sized battery can operate for about one hour.

In reality, however, the efficiency of the small pressure oscillation generating devices disclosed herein can be notably higher (as sound fidelity is not an issue in such devices). Moreover, since we expect the device to work with a typical duty cycle of a few 10% (as the subwoofer 402 was used), the small pressure oscillation generating devices disclosed in the present application will be able to operate for several hours until the battery (or other power source being used) runs out.

Figure 33:
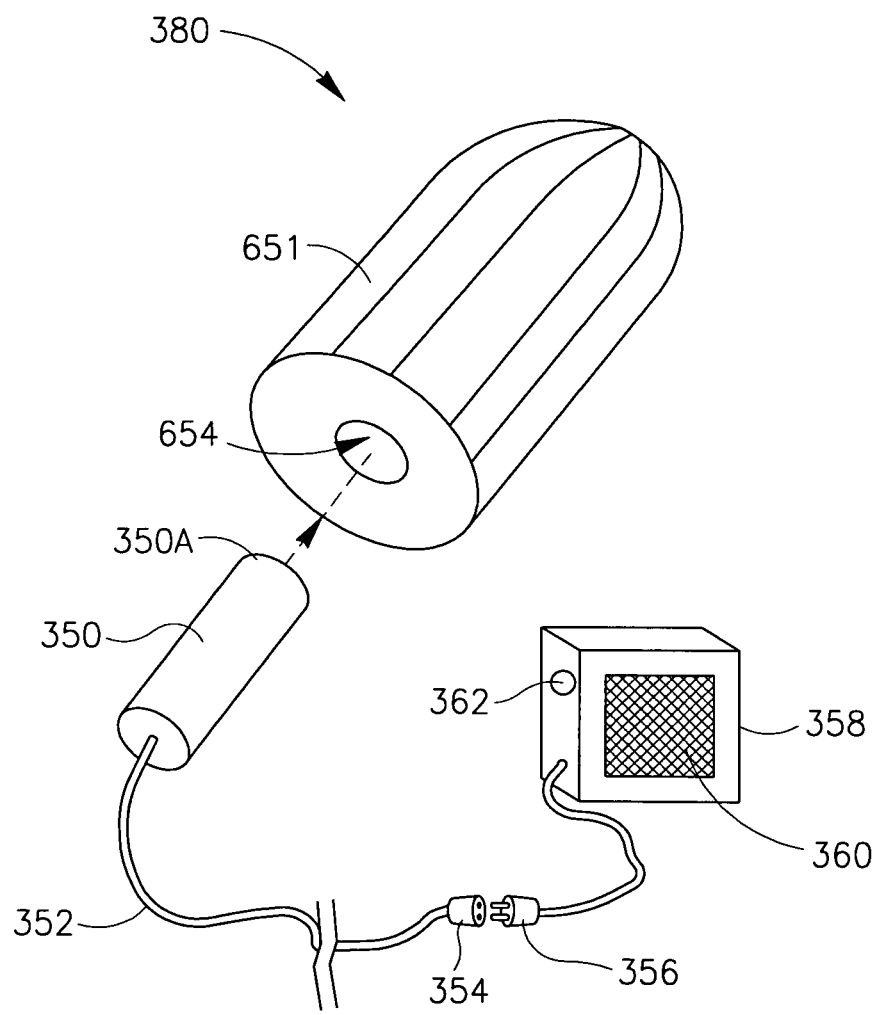
FIG. 33 is schematic isometric view illustrating a system for shortening menstruation period duration having a reusable pressure oscillations generating unit and disposable tampon-like absorbent sleeves configured to be detachably attached to the pressure oscillations generating unit, in accordance with an embodiment of the menstruation period shortening systems of the present application.

Reference is now made to FIG. 33 which is schematic isometric view illustrating a system for shortening menstruation period duration having a reusable pressure oscillations generating unit and disposable tampon-like absorbent sleeves configured to be detachably attached to the pressure oscillations generating unit, in accordance with an embodiment of the menstruation period shortening systems of the present application.

The system 380 includes a pressure oscillations generating device 350 which may be implemented as any of the devices 220, 250, 270 and 300 disclosed hereinabove or as any other small efficient device capable of delivering pressure oscillations of the required power to the vagina. The pressure oscillations generating device 350 may be electrically coupled through a suitable, electrically isolated power cord 352 to an external power source 358, designed to be disposed outside the vagina during use of the system 380. The power cord 352 may (optionally) have a connector 354 for connecting to a second connector 356 which is electrically connected to the power source 358. The power source 358 may be a small power source attachable to the skin of the user in the region of the upper thigh or the pelvis of the user by a suitable adhesive patch 360 attached to the power source 358. Alternatively, the power source 358 may be attached to a belt (not shown) or a garment (not shown) worn by the user, either by the adhesive patch 360 or by a similar patch of Velcro® or the like. The power source 358 may be controlled by a suitable switch 362 as illustrated. The power source may be any suitable electrical power source known in the art, such as but not limited to, a battery, an electrochemical cell, a primary electrochemical cell, a rechargeable electrochemical cell, a super-capacitor, a fuel cell and any combinations of any number of the above described power sources.

The system 380 also includes one or more absorbent members 651. The specific (non-limiting) illustrated example of the absorbent member 651 is shaped as a tampon-like absorbent member which is sleeve-like. The sleeve-like absorbent member 651 has a hollow passage 654 passing therethrough. In use, the pressure oscillations generating device 350 is inserted into the passage 654 of the sleeve-like absorbent member 651 such that the end 350A of the pressure oscillations generating device 350 which is configured to generate the pressure oscillations, is inserted in the direction shown by the arrowhead. After the sleeve-like absorbent member 651 is fitted onto the pressure oscillations generating device 350, and the sleeve-like absorbent member 651 together with the pressure oscillations generating device 350 attached thereto are inserted into the vagina and the pressure oscillations may be applied by switching on the switch 362.

The menses will be absorbed by the sleeve-like absorbent member 651. At any desired time during the use of the system 380, the user may take the sleeve-like absorbent member 651 and the pressure oscillations generating device 350, remove the used absorbent member and fit a fresh unused sleeve-like absorbent member 651 onto the pressure oscillations generating device 350, for reinsertion into the vagina. The pressure oscillations generating device 350, is configure to be completely impervious to liquids, such that it may be cleaned by washing after being removed from the vagina.

The present application also contemplates a kit which includes the pressure oscillations generating device 350 and several sleeve-like absorbent members 651 packed together. The kit may (optionally) also include the power source 358.

In accordance with another embodiment of the systems of the present application, the power source 358 may be a large power source with replaceable batteries or electrochemical cell(s) and or rechargeable power source with rechargeable cell(s) which may be attached to a belt (not shown) worn by the user. The power source 358 may be a rechargeable power source which may be conveniently recharged by the user.

Figure 36:
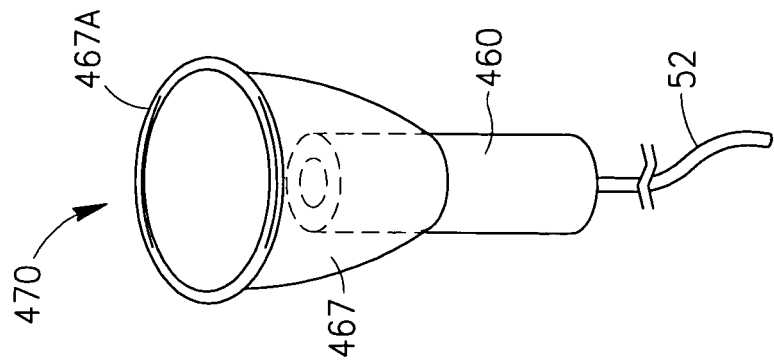
FIG. 36 is a schematic perspective view illustrating a vaginal pressure oscillations generating unit including a menses collecting member, in accordance with yet another embodiment of the menstruation period duration shortening device of the present application.
Figure 35:
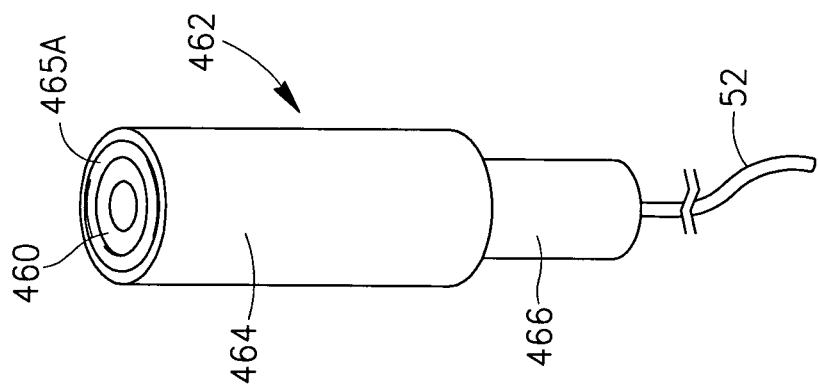
FIG. 35 is a perspective view of the vaginal pressure oscillations generating unit of FIG. 34 folded within an insertion device usable for introducing the pressure oscillations generating unit into a vagina.
Figure 34:
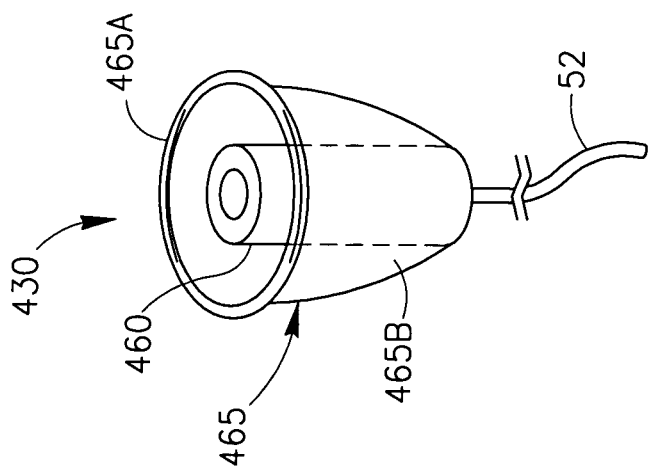
FIG. 34 is a schematic perspective view illustrating a vaginal pressure oscillations generating unit including a menses collecting member, in accordance with another embodiment of the menstruation period duration shortening device of the present application.

Reference is now made to FIGS. 34-36. FIG. 34 is a schematic perspective view illustrating a vaginal pressure oscillations generating unit including a menses collecting member, in accordance with another embodiment of the menstruation period duration shortening device of the present application. FIG. 35 is a perspective view of the vaginal pressure oscillations generating unit of FIG. 34 folded within an insertion device usable for introducing the vaginal pressure oscillations generating unit into a vagina. FIG. 36 is a schematic perspective view illustrating a vaginal pressure oscillations generating unit including a menses collecting member, in accordance with yet another embodiment of the menstruation period duration shortening device of the present application.

The vaginal pressure oscillations generating unit 430 of FIG. 34 includes a cylindrical pressure oscillations generating unit 460 which may be any of the devices 220, 250, 270 and 300 disclosed hereinabove or any other small efficient device capable of delivering pressure oscillations of the required power to the vagina as is disclosed hereinabove. The pressure oscillations generating unit 460 is attached at the closed end of a cup-like menses collecting member 465. The menses collecting member 465 is similar in shape to commercial menses collecting cups, as is known in the art. The menses collecting member 465 includes a soft thin walled elastic cup-like portion 465B and a thicker elastic ring-like portion 465A. For example, the menses collecting member 465 may be made from latex or from any other suitable elastic biocompatible material, such as an elastic polymer, or the like. A suitable pulling cord 52 may be attached at the bottom end of the menses collecting member 465 as illustrated for assisting the pulling out of the device from the vagina.

The vaginal pressure oscillations generating unit 430 of FIG. 34 may be inserted into the vagina by using a suitable insertion device 462. The insertion device 456 may include two disposable cardboard or plastic tubes 464 and 466. The plastic tube 466 has a smaller diameter and is movably or slidably attached within the larger tube 464. The vaginal pressure oscillations generating unit 430 is disposed within the tube 464 with the menses collecting member 465 properly folded and the pulling cord 52 is inserted into the lumen of the tube 466. The entire insertion assisting member 462 is inserted into the vagina and the vaginal pressure oscillations generating unit 430 is then pushed further into the vagina by holding the tube 464 and pushing the narrower tube 466 forward to push the vaginal pressure oscillations generating unit 430 outside the tube 464. The menses collecting member 465 unfolds and is pushed to fit over the cervix. The tubes 464 and 466 may then be taken out of the vagina and discarded. The application of pressure oscillations to the vagina and/or cervix by the pressure oscillations generating unit 460, may be done in any of the ways disclosed hereinabove and the menses collects in the menses collecting member 465. The vaginal pressure oscillations generating unit 430 may be pulled out from the vagina by using the pulling cord 52.

In accordance with another embodiment of the device including a menses collecting member, the position of the menses collecting member in relation to the pressure oscillations generating unit may be different.

Turning to FIG. 36, the vaginal pressure oscillations generating unit 470 includes the cylindrical pressure oscillations generating unit 460 of FIG. 34. The pressure oscillations generating unit 460 is attached to a cup-like menses collecting member 467. The menses collecting member 467 is similar in shape to commercial menses collecting cups, as is known in the art but has an opening at its bottom end. The menses collecting member 467 is sealingly attached to the middle portion of the pressure oscillations generating unit 460 by suitable attachment method, such as but not limited to, gluing or sealing with a suitable biocompatible glue or sealant, as is illustrated in FIG. 36. This embodiment of the device 470 increases the distance from the active end of the pressure oscillations generating unit 460 and the cervical external os.

Figure 37:
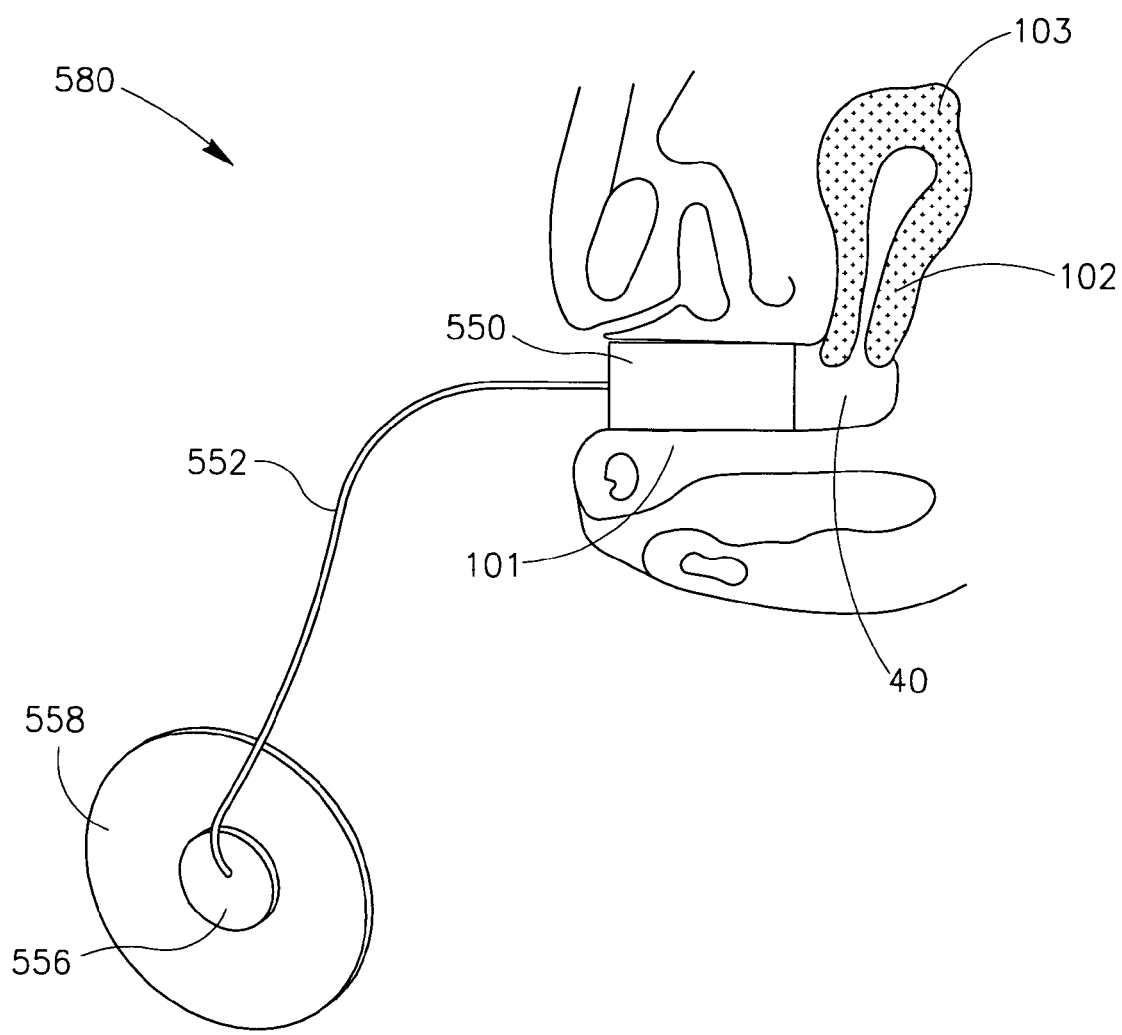
FIG. 37 is a schematic cross sectional view illustrating a vaginal pressure oscillations generating unit without an absorbing member disposed within a vagina, in accordance with still another embodiment of the menstruation period duration shortening device of the present application.

Reference is now made to FIG. 37 which is a schematic cross sectional view illustrating a vaginal pressure oscillations generating unit without an absorbing member disposed within a vagina, in accordance with still another embodiment of the menstruation period duration shortening device of the present application.

The device 580 includes a cylindrical pressure oscillations generating unit 550 which may be any of the devices 220, 250, 270 and 300 disclosed hereinabove (which are modified such that these devices do not include an internal power source) or any other small efficient device capable of delivering pressure oscillations of the required power to the vagina as is disclosed hereinabove. The device 580 of FIG. 37 is illustrated in a configuration having an external power source. The power source 556 is a small power source such as, but not limited to, any of the compact small power sources disclosed hereinabove, any small battery or electrochemical cell may be used as the power source 556, but other power sources disclosed hereinabove may also be used. The power source 556 is electrically connected to the pressure oscillations generating unit 550 by a suitable electrically isolated power cord 552. The power source 556 may be attached to the body of the user by an adhesive patch 558 (for example, the adhesive patch 558 may be attached to the upper thigh or the pelvis region of the user). Alternatively, the power source 556 may be attached to a garment (not shown) or to a belt (not shown) worn by the user. The, pressure oscillations generating unit 550 may be inserted into the vagina 101 of a user as disclosed hereinabove and the pressure oscillations may be activated remotely using any of the remotely actuatable switches (not shown) which may (optionally) be included in the pressure oscillations generating unit 550.

In accordance with another embodiment of the device 580 described hereinabove, the pressure oscillations generating unit 550 may be configured as a device having an internal power source, such as any of the devices 220, 250, 270 and 300 disclosed hereinabove. In the latter case, the power source 556, the power cord 552 and the patch become redundant and are not included. However, in such a case, the device may include a pulling cord (not shown in FIG. 37) attached at it's rear end (instead of the power cord 552) which may be similar to the pulling cord 52 illustrated in FIG. 17 and which used to facilitate the removal of the pressure oscillations generating unit 550 from the vagina 101.

It is noted that the pressure oscillations generating unit 550 of the device 580 may be operated within the vagina 101 without any absorbent member or tampon-like absorbing pad. For example, the user of the device 580 may use any type of commercially available external absorbing pads or other hygienic absorbing members placed outside of the user's vagina to absorb menses. Moreover, it is noted that the use of any absorbent member (whether an sleeve-like, tampon-like, or any other type of extra-vaginal or intra-vaginal absorbent member) is not necessary or obligatory to the successful and efficient operation of the devices and systems disclosed herein and that such devices may be operated effectively without the use of any absorbent member whatsoever.

It is noted that the design and implementations of the various different embodiments pressure oscillations generating units disclosed hereinabove which are designed for producing pressure oscillations within a vaginal cavity arise from theoretical considerations following a detailed mathematical analysis of the physical mechanisms of operation of such devices showing that for typically available energies (as may be supplied by currently available compact batteries or other compact power sources), the pressure gradient oscillation generated by the pressure oscillations generating units described herein is sufficient to trigger the physical effects which increase the rate of menses flow through the cervix, while for other devices such as regular vibrators which rely only on waves propagating in the vaginal tissues, the energy delivered would be insufficient for obtaining a significant increase in the rate of menses flow through the cervix by an order of magnitude. The theoretical analysis is attached hereinafter as APPENDIX A.

It is noted that the devices systems, and methods disclosed herein are not limited to the specific menses duration shortening application described. The devices, systems and methods disclosed in the present application are based on a concept of applying pressure oscillations to non-Newtonian fluids, and pertain to the various medical and therapeutic effects that can be achieved through the application of shear and vibrational thinning to induce streaming on various cavities and lumens of the human body.

The sinuses and their thin long connecting tubes, the intestine, the bladder, the arteries, the veins and the uterus, are all examples of cavities and lumens of the human body that may be affected in various ways by the use of the devices and the methods disclosed herein. The common effect of applying cyclic energy, according to the present invention, to these cavities and lumens, is to eliminate or to evacuate from them naturally occurring or dysfunctionally created obstructions or limiting particles that intervene with the natural flow of bodily substances in that cavities or lumen.

For example, constipation is a well known dysfunction which is treated with a wide variety of medications. The devices systems and methods disclosed hereinabove, may also be adapted with suitable modifications to obtain painless, non-medication related, invasive and easy evacuation of the intestine. This is achieved by creating the vibrational thinning effect.

Similarly, the pressure oscillations generating devices disclosed herein may be used for increasing the rate of removal of any non-Newtonian fluid or secretion from within a body passage which is naturally or pathologically congested with such secretions by using the same devices, principles and methods based on the physical phenomena disclosed hereinabove with respect to the particular non-limiting example with respect to menses in menstruating females. Such body passages may include, but are not limited to, congested nostrils and/or nasal cavities, congested parts of the gastrointestinal tract, constipated colon, any congested parts of the urinary tract of males and females, various parts of the respiratory canal such as but not limited to lungs, larynx bronchi, trachea, passages within the auditory system, such as but not limited to the external acoustic meatus, the pharingotympanic (auditory) tube, or other passages within the ear and other congested body passages and cavities.

It is noted that in principle, it is expected that the shortening of the duration of contact between the menses with the walls of the uterus resulting from the faster removal of menses from within the uterus may also result in reducing the pain, and/or cramps associated with dysmenorrhea in users who do suffer from dysmenorrhea.

Although the invention has been described in conjunction with specific embodiments thereof, it would be clear that many alternatives, modifications, permutations and variations of the devices, methods, systems and kits described herein will be apparent to those skilled in the art. Accordingly, it is intended to embrace all such alternatives, modifications, permutations and variations that fall within the spirit and broad scope of the appended claims.

APPENDIX A

Analysis of the Physical Mechanism of the Period Shortening Device

1 Goal

The aim of this appendix is to analyze the physical mechanism of the device of the present application. In particular, we wish to show that the main effect is achieved by means of an oscillating pressure gradient across the cervix and that under realistic conditions a standard sized battery can supply the necessary energy. On the other hand, vibrating the cervix through waves propagating from vibrating vaginal tissue is negligible when compared with the effects of a variable pressure gradient, and by itself, would have been insufficient to facilitate the flow of menses through the cervix. In other words, the proposed idea of generating pressure oscillations in the device is the sole reason for its efficacy.

2 Background

Before concentrating on the details of the physics behind the device, we begin with a short summary of how the device works.

Figure 38:
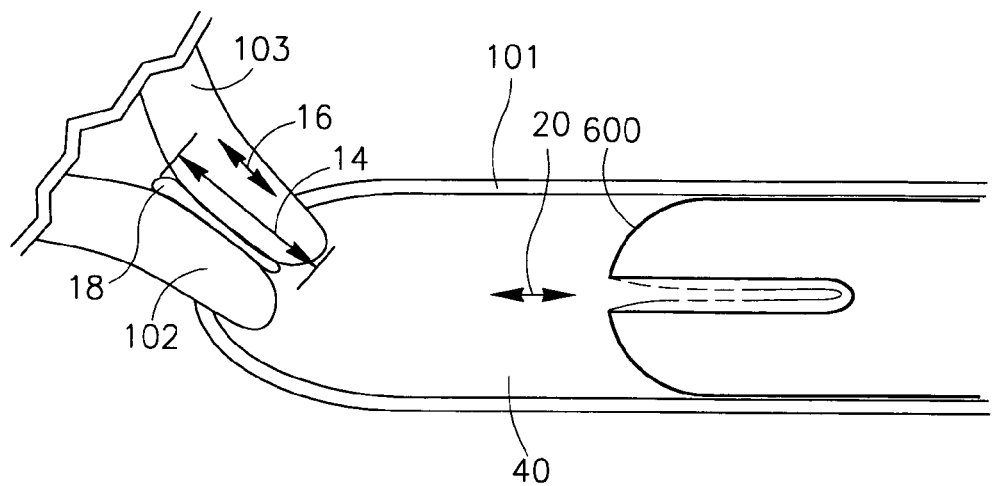
FIG. 38 is a schematic cross sectional view illustrating a vaginal pressure oscillations generating unit disposed within a vagina and useful in understanding the theoretical analysis of APPENDIX A.

The device and its setting are described in FIG. 38. The device, denoted by 600 in the figure, is inserted into the vagina. It is held in place by the vaginal tissue, denoted by 101 in the figure (in the same way the tissue holds a menstrual cup or a tampon). This forms an artificial cavity, denoted as 40 in the figure, between the device, the vaginal tissue and the cervix, which is marked as 102. When the device operates, an oscillating membrane periodically pushes air (or fluid) into and out of the device, as denoted by the double arrow 20. Because of the finite elasticity of the vaginal tissue, the cavity has a finite compliance implying that the changing amount of air/fluid in the cavity will change the pressure inside of it. The oscillating pressure in the cavity also implies that there is an oscillatory pressure gradient across the cervix, between the uterus, marked 103 and the artificial cavity 40, as exemplified by the double arrow 14 in the figure. This will accelerate the menses within the cervix, which are denoted as 18 in the figure. The finite elasticity of the vaginal tissue also implies that the walls oscillate in response to the oscillating pressure. (If the walls would have been totally rigid, then the cavity's pressure would have changed without inducing any wall movement). This generates elastic waves in the vaginal tissue. These waves can propagate through the tissue and reach the cervix. This will cause an oscillatory motion, as exemplified by the double arrow 16 in the figure. This oscillation will too accelerate the menses within the cervix. As shown below, the effects of the latter oscillations is negligible when compared to the direct pressure oscillations across the cervix.

3 The Forces on Menses within the Cervix

From FIG. 38 it is apparent that two forces can operate on the menses.

The first force is due to the pressure gradient $\nabla p$ across the cervix. This force per unit volume is given by $$F_{pres} = \nabla p = \frac{\Delta p}{l}, \quad (1)$$

where l~4 cm is the typical length of the cervix, and $\Delta p$ the total pressure drop across it.

The second force is the fictitious d'Alambert force. That is, we are interested in the motion of the menses relative to the cervix. However, because the cervix is vibrating, its frame-of-reference is constantly accelerating. In this frame, the menses will experience the following effective force (per unit volume):

$$F_{cervix} = \ddot{x}_c \rho \quad (2)$$

Here $\rho \approx 1$ gr/cm³ is the density of the menses. $\ddot{x}_c$ is the displacement of the cervix along the direction of its main axis such that $\ddot{x}_c$ is its acceleration. Since we assume for simplicity harmonic oscillations, we have $x_c = \alpha_c \cos \omega t$ with $\alpha_c$ being the amplitude. For the harmonic oscillations we also have that $\ddot{x}_c = -\omega_2 x_c$.

To estimate the amplitude at the cervix $\alpha_c$, we can use conservation of energy. If we assume an isotropic distribution, then the energy per unit area at some distance from the source should fall as the area, or distance squared. Since the energy of the harmonic waves is proportional to the amplitude squared, the amplitude of the waves should fall as the distance from the source. More specifically, we can estimate the ratio between the cervical amplitude and the amplitude at the outer edge of the vaginal cavity, $\alpha_v$ as:

$$a_c \sim a_v \sqrt{\frac{2\pi Rs}{4\pi L^2}}, \quad (3)$$

where L~5 cm, is the typical distance between the edges of the cavity and the cervix. The cavity is assumed to be a cylinder of R~1.5 cm and length s~2 cm. Note that this estimate of $\alpha_c$ is actually an overestimate for two reasons. First, only oscillations of the cervix along its axis are relevant for the facilitation of the flow, thus, we should consider only the oscillatory component in that direction. The second reason is the "impedance mismatching" of the elastic waves going from the vaginal tissue to the harder cervical tissue. That is, the oscillation of the cervix should be somewhat smaller than the oscillation of the vaginal tissue.

To estimate the the amplitude a of the vaginal wall displacement: $x_v = \alpha_v \cos \omega t$, we have to model the oscillations of the vaginal walls. To do so, we compare the system to an harmonic oscillator. The mass participating in the oscillations is roughly the tissue mass that would have been in the cylinder forming the cavity, i.e., $M \sim \pi \rho R^2 s$. Note that we assume all tissue to have $\rho \approx 1$ gr/cm³.

Next, if we compress the tissue radially by $x_v$, then the cost of elastic energy is of order $U_{elastic} \sim VE(x_v/R)^2/2$, where E~100–300 kPa is the expected elastic modulus for the combined stretching and compressing of the fibromuscular vaginal tissue, and V is the volume participating in the tissue distortion, which is roughly $V \sim \pi R^2 s$. Thus, the elastic force is of order $F_{elastic} = -dU_{elastic}/dx_v \sim -\pi E \alpha_v s$.

We also have to include, however, the force from the pressure within the cavity, which is $F_{cavity} = A\Delta p \sim 2\pi R s \Delta p$ (with A being the cavity's area). Therefore, if we neglect for a moment the dissipation, then the equation of motion of the mass will be:

$$M\ddot{x}_v = F_{elastic} + F_{cavity} \Rightarrow \pi R^2 s \ddot{x}_v \rho \approx -\pi E s x_v + 2\pi R s \Delta p \quad (4)$$

If we consider that $x_v = \alpha_v \cos \omega t$, such that $\ddot{x}_v = -\omega_2 x_v$, we obtain $$a_v \approx \frac{2R\Delta p}{E + \rho R^2 \omega^2}. \quad (5)$$

Note that formally for the undamped oscillator, the sign in the denominator should have been a "−". This would have meant that at a critical frequency there would be a resonance for the tissue motion. This would have been an unrealistic artifact of the simple model. In reality, the tissue has a large damping coefficient such that the energy in the oscillation is typically lost over one cycle, from both a hysteresis effect and the generation of elastic waves (see §4 below). Thus, to get a realistic behavior for the amplitude we write a "+" instead.

Consequently, we can now relate the amplitude of the force due to the pressure gradient to the amplitude of the force due to the vibrations of the cervix, we find:

$$\frac{F_{cervix}}{F_{pres}} \approx \frac{\rho a_c \omega^2}{\Delta p / l} \approx \sqrt{\frac{2Rs}{L^2}} \frac{\rho R l \omega^2}{\omega^2 \rho R^2 + E}. \quad (6)$$

We see that there are two limits, which cross over at $\omega_{cross} \sim \sqrt{E/\rho R^2}$. For our nominal values $\omega_{cross} \sim 1$ ksec⁻¹, or a frequency $f_{cross} \sim 150$ Hz.

For low frequencies, we find:

$$\frac{F_{cervix}}{F_{pres}} \approx \sqrt{\frac{2sl^2}{L^2 R} \frac{\rho R^2 \omega^2}{E}}. \quad (7)$$

Since the term under the root sign is of order unity, we have in this limit that:

$$\frac{F_{cervix}}{F_{pres}} \sim \left(\frac{f}{f_{cross}}\right)^2 \sim 0.1 \text{ for } f \sim 50 \text{ Hz}. \quad (8)$$

In the opposite limit we have:

$$\frac{F_{cervix}}{F_{pres}} \sim \sqrt{\frac{2l^2 s}{L^2 R}} \sim 1. \quad (9)$$

Namely, for high frequencies, the two contributions to the force are comparable. However, this happens for frequencies where both contributions cannot induce any significant effect in any case (as elaborated in §5 below).

4 Amplitudes for a given supplied power

To obtain the oscillation amplitude, we have to consider that the device generates pressure oscillations within the cavity with some given power $P_{tot}$. This will itself be the device's power multiplied by the efficiency of the device $\epsilon$. From battery constraints, while considering a conservative 10% efficiency, we can typically expect $P_{tot}$=0.1 Watt.

The power going into the pressure oscillations will transfer energy to the tissue and then get dissipated there. There are two primary dissipation methods, one is through elastic waves and the second is through local dissipation (caused by the hysteresis behavior of the tissue).

The first term is:

$$P_{hyster} = \frac{\alpha U_{elastic}}{T} \approx \frac{\alpha}{4} \omega E s a_v^2 \quad (10)$$

where $U_{elastic}$ is the elastic energy associated with the oscillation, T is the period of oscillation while $\alpha \sim 0.5$ is the fraction of energy lost per cycle.

The second term is:

$$P_{wave} \approx \rho A \alpha_v^2 \omega^2 v_e \approx 2\pi \rho^{1/2} R s \omega^2 E^{1/2} \alpha_v^2. \quad (11)$$

Here $v_e \sim \sqrt{E/\rho}$ is the speed of elastic waves, and A is the surface area where the waves are generated.

At about 30 Hz, the two contributions are comparable.

In our system, the power generated by the device becomes the pressure oscillations, which in turn transfer the energy to oscillations of the tissue which is then lost as either waves or in the hysteresis of the tissue. Namely, $P_{tot} = \epsilon P_{device} = P_{wave} + P_{hyster}$.

This implies that the amplitude of oscillations of the vaginal walls is $$a_v \approx \sqrt{\frac{P_{tot}}{2\pi \rho^{1/2} R s \omega^2 E^{1/2} + \alpha \omega E s/4}}. \quad (12)$$

This allows us to calculate $\alpha_c$ and $\Delta p/l$.

For convenience, we can define an amplitude which is the amplitude that the cervix should equivalently have for it to induce the same force as the pressure gradient, that is, $$a_p \equiv \frac{\Delta p/l}{\rho \omega^2}, \quad (13)$$

such that $F_{cervix}/F_{pres} = \alpha_c/\alpha_p$.

Using this notation we have:

$$a_p = \frac{F_{pres}}{\rho \omega^2} \approx \frac{\rho \omega^2 R^2 + E}{l\rho \omega^2} \sqrt{\frac{P_{tot}}{2\pi \rho^{1/2} R s \omega^2 E^{1/2} + \alpha \omega E s/4}} \quad (14)$$

and also $$a_c \approx \sqrt{\frac{Rs}{2L^2}} \sqrt{\frac{P_{tot}}{2\pi \rho^{1/2} R s \omega^2 E^{1/2} + \alpha \omega E s/4}}. \quad (15)$$

5 Threshold amplitudes

Is the amplitude of oscillation sufficient to trigger an effect which will facilitate the flow of menses through the cervix? To answer this question we have to calculate the threshold amplitudes required for the different effects. Here we summarize the threshold amplitudes in terms of the necessary amplitude of oscillation of the cervix or the equivalent amplitude for the pressure oscillations. These results are based on the work of Uriev [1] which is based on both theoretical and experimental analyses.

Following Uriev, it is evident that the viscosity can be reduced as a response to two related effects. One is through the development of shear in the flow and can occur without vibrations, the second is due to vibrations and which can occur without any shear. Either effects can independently reduce the effective viscosity. There is also a threshold amplitude above which the acceleration exceeds that of gravity and allows for the resettling and "unclogging" of the inner cervical os from tissue debris.

Shear reduction of the viscosity—$\alpha_\gamma$: Given the results of Uriev [1], a large enough amplitude of oscillation will give rise to a shear (a gradient in the velocity field that is perpendicular to the velocity itself) which will be able to reduce the viscosity of the menses within the cervix. However, because the velocity depends on the flow, we have to consider that there are two types of flow behavior. For low frequencies, the force accelerates the fluid until it reaches a velocity limited by the viscosity. At high frequencies, this limiting velocity cannot be reached because the inertia of the fluid limits it. The two behaviors are encapsulated with the approximate threshold amplitude:

$$a_\gamma \approx \frac{2\dot{\gamma}_c \eta_0}{\rho r \omega^2}\left(1 + \frac{r^2 \rho \omega}{\eta_0}\right) \quad (16)$$

where r is the cervical radius, $\eta_0$ is the effective viscosity of the fluid, which we measured to be ~5 poise, and $\dot{\gamma}_c$ is the threshold shear to get an effect:

$$\dot{\gamma}_c \approx \frac{\eta_f}{\rho d^2} \qquad (17)$$

Here $\eta_f \sim 0.1$ poise is the viscosity of the fluid without the debris (i.e., similar to blood). $d \sim 0.1$ cm is the typical smallest debris size.

Vibrational reduction of the viscosity—$\alpha_\omega, \alpha_d, \alpha_\sigma$: Viscosity reduction can also take place through vibrations. Basically, in the frame of reference of the oscillating fluid, debris particles experience a periodic force. If they can vibrate to distances larger than their typical size, then the fluid viscosity is reduced, as it will allow the debris to self-organize in response to the flow. This has two constraints which capture the two limits whether the debris inertia is important or not. Irrespectively, there is a third constraint that the surface tension will not force the particles to stick together. Thus, for this effect to take place, the vibrational amplitude has to be larger than the following three amplitudes:

$$a_\omega \approx \frac{\eta_f}{\rho d \omega}, a_d \approx d, a_\sigma \approx \frac{f_\sigma \sigma}{\rho d^2 \omega^2} \qquad (18)$$

where $f_o$ is the fraction of the particles's surface are which is actually in contact with other particles. $\sigma$ is the surface tension.

Gravitational resettling amplitude—$\alpha_g$: If the acceleration associated with the vibrations is larger than g, then gravitational resettling can occur and "unclog" debris residing in the inner cervical os. This requires that $\alpha_r > \alpha_o$ defined above and also:

$$\alpha_g \approx g/\omega^2 \qquad (19)$$

5.1 Amplitude comparison

Figure 39:
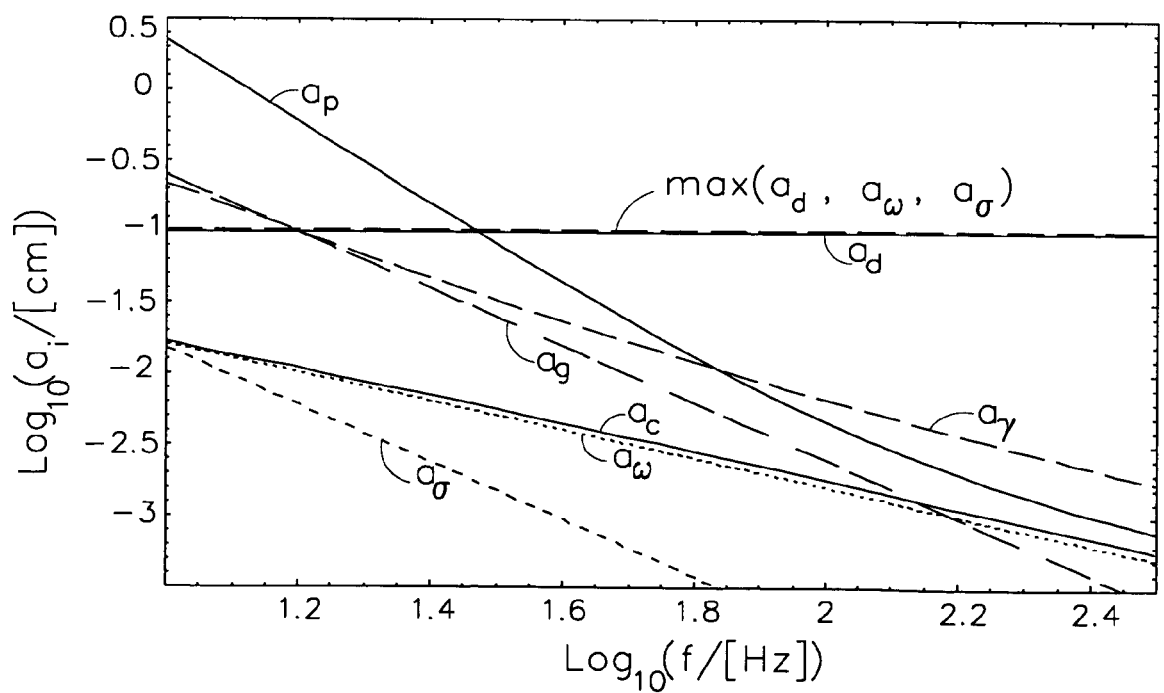
FIG. 39 is a schematic graph illustrating the menses excitation amplitude as a function of the pressure oscillation frequency, as theoretically computed in APPENDIX A for nominal parameters and an assumed pressure oscillation power of 0.1 Watt.

The different excitation and threshold amplitudes are plotted in FIG. 39 as a function of the applied pressure oscillation frequency, for nominal parameters defined in §3-5 while assuming that the energy going into the pressure oscillations is 0.1 Watt. The amplitudes are $\alpha_p$, the effective amplitude that the cervix oscillations should equivalently have to give rise to the same acceleration of the menses as the pressure gradient across the cervix, and $\alpha_c$, which is the actual amplitude of the cervical oscillations from the elastic waves. The other amplitudes are the threshold amplitudes needed to satisfy different criteria. $\alpha_\gamma$ is (he amplitude above which the shear in the flow is sufficient to reduce the effective viscosity. $\max(\alpha_d, \alpha_\omega, \alpha_\sigma)$ is the threshold amplitude above which vibrations can reduce the effective viscosity. It is composed of several thresholds, all of which should be surpassed for the effect to take place. Last $\alpha_g$ is the amplitude above which the acceleration surpasses g and allows for gravitational resettling. For the nominal parameters, there is an effect only from the oscillatory $\Delta p$, up to about 80 Hz. On the other hand, there is no reasonable range of values for which $\alpha_c$ rises above any threshold amplitude unless the input power is about an order of magnitude higher.

If we conservatively assume a 10% efficiency, this power implies that a 1000 mWhr battery (or other compact energy source) can operate the device continuously for 1 hr, or several hours assuming a finite duty cycle.

6 Summary

The device device generates pressure oscillations in the cavity between the device and the cervix and also generates waves in the vaginal tissue as a secondary effect.

For frequencies below of order 150 Hz, the primary effect of vibrating the menses within the cervix is through the variable pressure drop across the cervix. At 50 Hz, for example it is at least 10 times larger than the effect of elastic waves propagating through the vaginal tissue.

An analysis has shown that for the typically available energies, the pressure gradient oscillation is sufficient to trigger the effects modifying the menses flow through the cervix. On the other hand, if the device was to rely only on the waves propagating in the tissue, the energy would have been insufficient by an order of magnitude.

Modification of the menses rheology takes place below 50-100 Hz (depending on the actual parameters). At very low frequencies, the amplitudes become too large (they would be noticeable by the patient, and also induce non-linear effects which were hitherto neglected). Thus, the optimal frequencies from this analysis appear to be around 30-50 Hz.

References

[1] N.B. Uriev. Physicochemical dynamics of disperse systems. Russian Chemical Reviews, 73:37-58, 2004.

The invention claimed is:

1. A device comprising:
a pressure oscillations generating unit having a housing and a membrane sealingly connected to said housing, said pressure oscillation generating unit being sized and shaped to be inserted into a vaginal chamber in a position that allows applying pressure oscillations via the vaginal air chamber thereinfront to a uterine cervix;
wherein said pressure oscillations are pressure waves generated by movement of said membrane; wherein said pressure waves oscillate along a general direction of a longitudinal axis of said pressure oscillations generating unit said membrane is a moveable elastic membrane sealingly attached to said housing of said pressure oscillations generating unit and coupled to a motor attached to said housing.

2. The device according to claim 1 wherein said device also comprises an absorbent member attached to said pressure oscillations generating unit for absorbing menstrual secretions.

3. The device according to claim 2 wherein said absorbent member is a sleeve like absorbent member attached to said pressure oscillations generating unit wherein said device is disposable.

4. The device according to claim 2 wherein part of said pressure oscillations generating unit and absorbent member is detachable and disposable and another part is reusable.

5. The device according to claim 1 wherein said device comprises a power source for energizing said pressure oscillations generator unit, said power source is selected from an internal power source disposed within said device and an external power source disposed outside said device and coupled to said pressure oscillations generator unit.

6. The device according to claim 5 wherein said power source is an electrical power source.

7. The device according to claim 1 wherein said pressure oscillations comprise pressure oscillations having a frequency in the range of 0.1 Hz-1 Hz, or in the range of 30 Hz-60 Hz.

8. The device according to claim 1 wherein said pressure oscillations generating unit is configured to deliver pressure oscillations having a power in the range of 0.01-1.0 Watt delivered via the vaginal air chamber thereinfront to said uterine cervix.

9. The device according to claim 1 wherein said pressure oscillations are applied via a chamber formed between said device and said uterine cervix.

10. The device according to claim 9 wherein said membrane is coupled to said chamber when said device is disposed in said vagina, said membrane is configured for delivering said pressure oscillations to said chamber.

11. The device according to claim 10 wherein said comprises a plurality of movable membranes sealingly attached to said housing, and connected to one or more permanent magnets; and wherein said magnets are located adjacent to an electrically activated coil.

12. The device according to claim 10, wherein said movable member is a membrane adapted to move at least 2 mm while causing a reduction in pressure in said vagina by said movement.

13. The device according to claim 1, wherein said device is configured such that said pressure oscillations generate a pressure gradient between said vagina and said uterus.

14. The device according to claim 1, wherein said device is configured such that said pressure oscillations liquefy menses.

15. The device according to claim 1, comprising a menses collector including a chamber configured to receive menses from said uterine cervix.

16. The device according to claim 1, mounted in an introducer.

17. The device according to claim 1 wherein one end of said movable elastic membrane faces an external side of a tampon.

18. The device according to claim 1 wherein said pressure oscillations generating unit generates non-ablating energy.

19. A method for evacuating a menses from a uterus of a female subject, the method comprises:
   applying pressure oscillations to a volume of fluid menses within the uterus of said female subject via a vaginal air chamber thereinfront to a uterine cervix, in a manner which increasing the rate of flow of menstrual secretions out of said uterus;
   wherein said pressure oscillations are pressure waves that oscillate along a general direction of a longitudinal axis of a pressure oscillations generating unit.

20. The method according to claim 19 wherein said applying comprises applying the pressure oscillations to fluid contained in a vaginal chamber defined between part of a pressure oscillations generating unit disposed within said vagina, part of the walls of said vagina and the cervix of said female subject.

21. The method according to claim 19, wherein said method is applied enough to shorten a duration of a menstruation period of said subject.

22. The method according to claim 19, wherein said pressure oscillations are applied from outside the body.

23. The method according to claim 19, wherein said pressure oscillations are applied using a totally inserted device.

24. The method according to claim 19, comprising generating a pressure gradient across a uterine cervix of said subject.

25. The method according to claim 19, comprising liquefying said menstrual secretions by said pressure oscillations.

26. The method according to claim 19, comprising introducing a pressure oscillations generating unit into said vagina to apply said oscillations.

27. A method for shortening menses duration, the method comprising:
   introducing into a vagina a device comprising a pressure oscillations generating unit for applying pressure oscillations to a uterine cervix in a position that allows applying pressure oscillations via the vaginal air chamber thereinfront to said uterine cervix; and
   activating said device to generate pressure oscillations within a vaginal chamber and traveling into said uterine cervix, thereby increasing the rate of flow of menstrual secretions out of said uterine cervix;
   wherein said pressure oscillations are pressure waves that oscillate along a general direction of a longitudinal axis of said pressure oscillations generating unit.

28. The method according to claim 27 wherein said activating comprises providing power to said pressure oscillations generating unit from a power source comprising
   an internal power source internally disposed within said device.

29. The method according to claim 27 wherein said activating comprises activating said pressure oscillations generating unit by remotely actuating an acuatable switching unit included in said device to provide power from said power source to said pressure oscillations generating unit.

30. The method according to claim 27 further including collecting menses fluids flowing into said vagina by a collector attached to said pressure oscillations generating unit.

31. The method according to claim 27 wherein said pressure oscillations comprises pressure oscillations having a frequency in the range of 0.1 Hz-1 Hz, or in the range of 30 Hz-60 Hz.

32. The method according to claim 27 wherein said pressure oscillations generating unit is configured to deliver pressure oscillations having a power in the range of 0.01-1.0 Watt delivered to said vaginal chamber.

* * * * *